(12) United States Patent
Haselton et al.

(10) Patent No.: US 10,101,323 B2
(45) Date of Patent: Oct. 16, 2018

(54) LIQUID DIAGNOSTIC ASSAYS UTILIZING MARANGONI FLOW

(71) Applicant: Vanderbilt University, Nashville, TN (US)

(72) Inventors: Frederick Haselton, Nashville, TN (US); Joshua R. Trantum, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 119 days.

(21) Appl. No.: 14/520,541

(22) Filed: Oct. 22, 2014

(65) Prior Publication Data

US 2015/0118696 A1    Apr. 30, 2015

Related U.S. Application Data

(60) Provisional application No. 61/894,678, filed on Oct. 23, 2013.

(51) Int. Cl.
    *G01N 33/543*     (2006.01)

(52) U.S. Cl.
    CPC ............... *G01N 33/54306* (2013.01)

(58) Field of Classification Search
    CPC ................................. G01N 33/54306
    See application file for complete search history.

(56) References Cited

U.S. PATENT DOCUMENTS

| | | | | |
|---|---|---|---|---|
| 5,812,312 A | * | 9/1998 | Lorincz ............... | G01N 1/30 359/396 |
| 6,951,716 B2 | * | 10/2005 | Hechinger ........... | C12Q 1/6816 435/4 |
| 2009/0215192 A1 | * | 8/2009 | Stolowitz ............. | B01J 19/0046 436/174 |
| 2010/0144059 A1 | * | 6/2010 | Frisk ................... | G01N 29/022 436/518 |

OTHER PUBLICATIONS

Fell et al., Influence of Surfactant Concentration and Background Salt on Forced Dynamic Wetting and Dewetting, Langmuir, 2011, 27 (6), pp. 2112-2117.*
Yap et al., Development of a slide latex agglutination test for rotavirus antigen detection, Malaysian J Pathol 1994; 16(1): 49-56.*
Grandien et al., Latex Agglutination Test for Adenovirus Diagnosis in Diarrheal Disease, Journal of Medical Virology 23:311-316 (1987).*
Drop. (2014). In Collins Dictionaries (Ed.), Collins English Dictionary (12th ed.). London, UK: Collins. Retrieved from https://search.credoreference.com/content/entry/hcengdict/drop/0?institutionId=743 3 pages.*
Droplet. (2014). In Collins Dictionaries (Ed.), Collins English Dictionary (12th ed.). London, UK: Collins. Retrieved from https://search.credoreference.com/content/entry/hcengdict/droplet/O?institutionId=743 1 page.*
Barash et al., "Evaporation and fluid dynamics of a sessile drop of capillary size",*Physical Review E.* , 79, (4), 2009.
Brutin et al., "Pattern formation in drying drops of blood", *Journal of Fluid Mechanics*, 667, 85-95, 2011.
Deegan et al., "Capillary flow as the cause of ring stains from dried liquid drops", *Nature*, 389, (6653), 827-829, 1997.
Deegan et al., "Contact line deposits in an evaporating drop", *Physical Review E*, 62, (1), 756-765, 2000.
Deegan, "Pattern formation in drying drops", *Physical Review E*, 61, (1), 475-485, 2000.
Hu et al., "Analysis of the effects of Marangoni stresses on the microflow in an evaporating sessile droplet", *Langmuir*, 21, (9), 3972-3980, 2005.
Hu et al., "Analysis of the microfluid flow in an evaporating sessile droplet",*Langmuir*, 21, (9), 3963-3971, 2005.
Hu et al., "Marangoni effect reverses coffee-ring depositions", *Journal of Physical Chemistry B*, 110, (14), 7090-7094, 2006.
Manukyan et al., "Imaging internal flows in a drying sessile polymer dispersion drop using Spectral Radar Optical Coherence Tomography (SR-OCT)", *Journal of Colloid and Interface Science*, 395, 287-293, 2013.
Ristenpart et al., "Influence of substrate conductivity on circulation reversal in evaporating drops", *Physical Review Letters*, 99, (23), 2007.
Sangani et al., "Capillary force on particles near a drop edge resting on a substrate and a criterion for contact line pinning", *Physical Review E*, 80, (1), 2009.
Savino et al., "Buoyancy and Marangoni Effects in an Evaporating Drop", *Journal of Thermophysics and Heat Transfer*, 16, (4), 562-574, 2002.
Still et al, "Surfactant-induced Marangoni eddies alter the coffee-rings of evaporating colloidal drops", *Langmuir*, 28, (11), 4984-4988, 2012.
Tarasevich & Pravoslavnova, "Drying of a rindticompoilent solution drop on a solid substrate: Qualitative analysis", *Technical Physics*, 52, (2), 159-163, 2007.
Tarasevich & Pravoslavnova, "Segregation in desiccated sessile drops of biological fluids", *European Physical Journal E*, 22, (4), 311-314, 2007.
Trantum et al., "Biomarker-mediated disruption of coffee-ring formation as a low resource diagnostic indicator", *Langmuir*, 28, (4), 2187-2193, 2012.

(Continued)

*Primary Examiner* — Andrea S Grossman
(74) *Attorney, Agent, or Firm* — Parker Highlander, PLLC

(57) ABSTRACT

The present invention provides simple and inexpensive assays for the detection of virtually any analyte in any sample that is in liquid form or that can be solubilized. The assays utilize the fluid dynamics of drop evaporation whereby soluble materials, including analytes and particles binding thereto, are drawn to the center of the drop by Marangoni flow and ultimately form a concentrated residual spot. The presence or absence of certain reagents can then be detected through a number of different approaches.

18 Claims, 6 Drawing Sheets

(56) References Cited

OTHER PUBLICATIONS

Trantum et al., "Biosensor design based on Marangoni flow in an evaporating drop", *Lab Chip*, 14: 315-324, 2014.
Trantum et al., "Cross-Sectional Tracking of Particle Motion in Evaporating Drops: Flow Fields and Interfacial Accumulation", *Langmuir*, 29, (21), 6221-31, 2013.
Widjaja and Harris, "Particle deposition study during sessile drop evaporation", 54(9): 2250-2260, 2008.
Wong et al., "Nanochromatography driven by the coffee ring effect", *Analytical Chemistry*, 83, (6), 1871-1873, 2011.

* cited by examiner

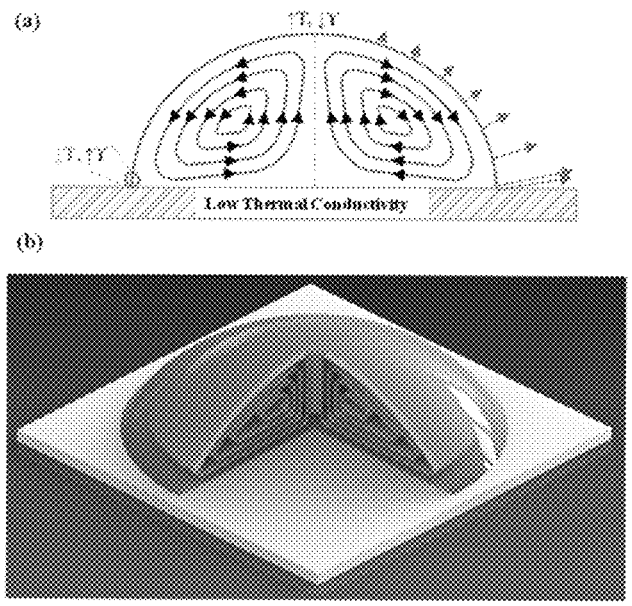
FIGS. 1A-B
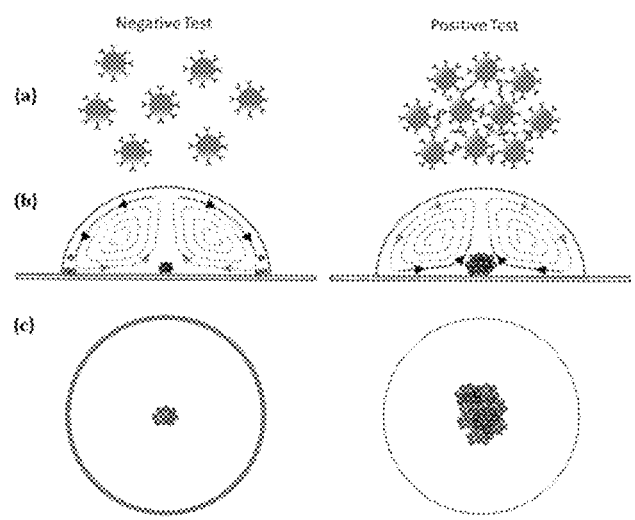
FIGS. 2A-C

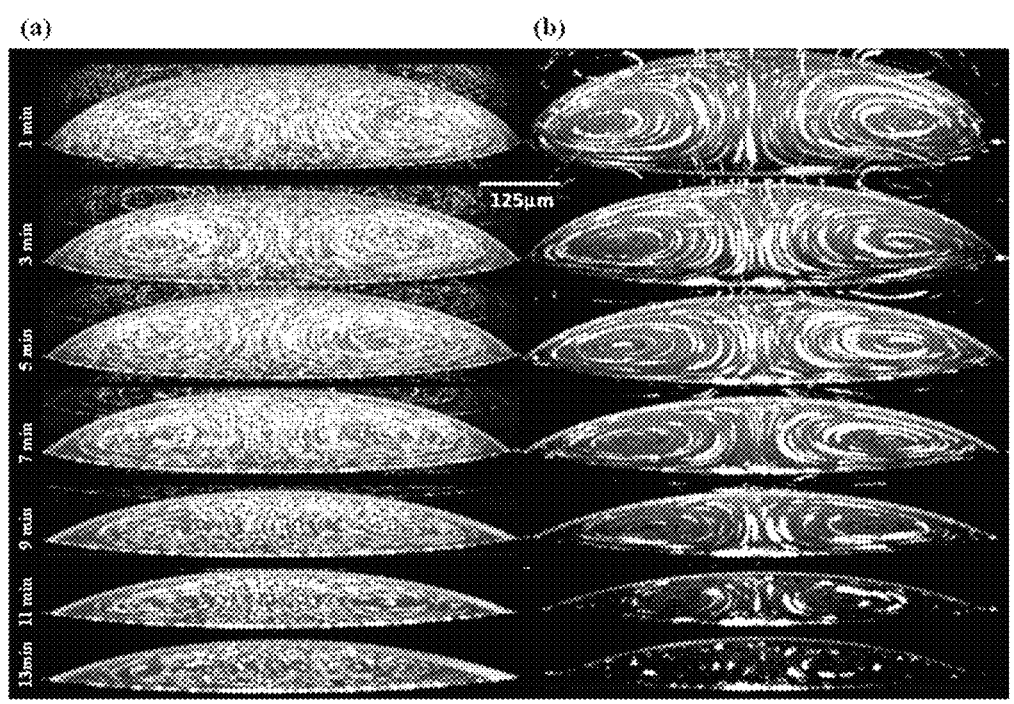
FIGS. 3A-B

FIGS. 5A-D

LIQUID DIAGNOSTIC ASSAYS UTILIZING MARANGONI FLOW

This application claims benefit of priority to U.S. Provisional Application Ser. No. 61/894,678, filed Oct. 23, 2013, the entire contents of which are hereby incorporated by reference.

This invention was made with government support under grant nos. R21 EB009235, R21 EY017552, and R21 HL095119, each awarded by the National Institutes of Health. The government has certain rights in the invention.

BACKGROUND OF THE INVENTION

I. Field of the Invention

The present invention relates to the fields of biology and diagnostics. More specifically, the invention deals with "drop"-based technologies that permit simple, fast and accurate detection of most any analyte in environmental, plant, medical and other samples.

II. Related Art

The engineering of diagnostic devices suitable for the low resource, point-of-care (POC) setting is challenged by design criteria that include low cost, simplicity of operation, and minimal reliance on external instrumentation (Yager et al., 2008 and Yager et al., 2006). The ideal biosensor requires no on-board power source and produces an easily detectable signal in a short period of time. Harnessing the hydrodynamics of an evaporating drop represents one possible means of satisfying these design requirements. Fluid motion inside an evaporating sessile drop occurs spontaneously due to a non-uniform evaporation rate along the surface of the drop, which produces predictable hydrodynamic properties (Deegan, 2000, Deegan et al., 2000 and Deegan et al., 1997). The resulting flow fields include the primary radial flow and secondary flows caused by direct and indirect effects of the non-uniform evaporation rate, respectively. (Deegan, 2000, Deegan et al., 2000, Deegan et al., 1997, Barash et al., 2009, Hu & Larson, 2005 and Hu & Larson, 2006).

The primary radial flow field is the most commonly and easily observed flow pattern and is what causes a ring to form in an evaporating coffee drop, known as the "coffee ring effect" (Deegan et al., 1997). The non-uniform evaporation rate across the surface of the drop induces a radial current that carries material in solution to the periphery of the drop resulting in a concentrated ring pattern (Deegan, 2000, Deegan et al., 2000, Deegan et al., 1997). A precondition for this hydrodynamic property is the presence of colloidal particles that pin the contact line preventing it from receding during evaporation (Deegan, 2000, Deegan et al., 2000, Sangani et al., 2009). Fluid flows in a radial direction to replenish solution preferentially lost at the edge where solvent molecules evaporate at the greatest rate. This naturally-occurring phenomenon is easily observed under a microscope with which the two-dimensional radial motion of micron-sized particles can be resolved. The physical basis and flow characteristics of this mass transport system have been previously described (Hu & Larson, 2005, Hu & Larson, 2005, Trantum et al., 2013, Hu & Larson 2005 and Harris & Widjaja, 2008).

Recently, several groups have reported using the primary radial flow to discern information about the components of the solution. Wong et al. demonstrated that the size exclusion geometry of the contact line in an evaporating drop can be used for chromatographic separation of colloidal particles (Wong et al., 2011). Several groups have shown that dried patterns of drops of biological fluids can be used to characterize sample components and potentially be used as an indicator of disease (Tarasevich & Pravoslavnova 2007a, Tarasevich & Pravoslavnova 2007b and Brutin et al., 2011).

The inventors recently reported a diagnostic assay in which the primary radial flow in an evaporating water drop organizes functionalized magnetic particles to generate a colorimetric response based on the presence of a biomarker (Trantum et al., 2012). This proof-of-concept assay successfully detected a peptide mimic of the malaria biomarker protein, *Plasmodium falciparum* histidine rich protein (pJHRP-II), using a Ni(II)NTA biorecognition element conjugated to the surface of the particles. Evaluation of this assay design reveals several limitations. First, the assay requires precise alignment of the drop over a magnetic field, operationally tedious for what is intended to be a simple and rapid assay. Second, the limit of detection, approximately 200 nM, must be at least 1000× more sensitive for clinical relevance in malaria detection. Finally, the assay does not work in the presence of salt at physiologic levels. Salt crystal formation at the end of the evaporation process significantly alters particle deposition patterns resulting in false results. Thus, even this improved approach would benefit from further improvements.

SUMMARY OF THE INVENTION

Thus, in accordance with the present invention, there is provided a method for detecting an analyte in a sample comprising (a) providing a sample in an aqueous liquid carrier, said liquid carrier also comprising (i) a salt or a sugar (ii) and a hygroscopic material/surfactant; (b) contacting said liquid sample with a capture particle that binds an analyte in said sample, wherein the presence of analyte results in the aggregation of said capture particles; (c) placing a droplet of said liquid sample in step (b) on a non-permeable substrate, wherein the thermal conductivity of the substrate is less than 1.6 times that of the liquid sample; and (d) incubating said substrate under conditions promoting inward Marangoni flow in said drop, wherein the presence of aggregated capture particles at said droplet center, as compared to a control assay lacking said analyte, reflects the presence of analyte in said sample. Steps (b) and (c) may be reversed in order.

The capture particles may comprise (i) a latex bead, a polystyrene bead, semi-conductor bead/quantum dot, a metal particle, a paramagnetic particle, or a superparamagnetic particle; and (ii) an analyte binding agent. The capture particles may further comprise an agent that reduces non-specific binding to other reagents. The analyte binding agent may be a protein, a chemical, a nucleic acid, a metal, or a carbohydrate. The protein may be an antibody, receptor, an antigen, or a fragment of any of the foregoing. The capture particles may be 1 nm to 100 μm in diameter, and/or may have a density of 1.001 gm/cm$^3$ to 20 gm/cm$^3$. The non-permeable substrate may be a plastic slide, a plastic rod, a plastic capillary tube, or a microarray pen. The non-permeable substrate may comprise polydimethylsiloxane. The analyte may be a protein, a nucleic acid, a toxin, a lipid, a carbohydrate, a drug or chemical, or a metal. The protein analyted may be a peptide, an antibody (to a pathogen, to a cancer antigen, to an autoantigen), an enzyme, a hormone, a pathogen antigen, a toxin, a cancer antigen, or a fragment of any of the foregoing. The liquid carrier may comprise water or organic solvent. The sample may be is a foodstuff, water, soil, plant material, a biopsy, bronchial lavage, nasal lavage, nasal swab, cheek swab, or a body fluid. The body fluid may be urine, spinal fluid, blood, plasma, serum, synovial fluid, mucous, occular fluid, sputum, saliva, or semen.

The method may further comprise washing said non-permeable substrate after step (d). The method may further comprise adding a detection agent that detects (i) said capture particle bound to said analyte at said droplet center or (ii) analyte at said droplet center. The method may further comprise use of a control particle that provides a positive control reaction.

The capture particles may exhibit a detectable change when aggregated, such as colorimetric, magnetic or spectrometric, and/or is precipitation of the particle onto the substrate. The capture particle may be labeled, such as with an enzyme, a fluorescent label, a chemilluminescent label, a radioactive label, or a colorimetric label. The label may permit amplification. The non-permeable substrate may be derivatized to bind said capture particle or said analyte. The hygroscopic material may be glycerol or LiCl; the surfactant may be Tween. The mixture of step (b) may be incubated for between 10 seconds and 24 hours prior to step (c). The capture particles may be located on said non-permeable substrate, and steps (b) and (c) are comprised in a single step of dropping said sample onto said non-permeable substrate.

Detection may comprise visual detection with the naked eye, or detection with a microscope and/or photographic device. Detection may comprise automated detection of a light, a fluorescent, a color or a radioactive signal associated with said capture particle, including quantitation of said signal. The droplet may form a spot of between 0.05 μm and 5000 μm, and/or the droplet volume may be between 0.1 μl to 100 μl. Multiple droplets may be placed on said substrate.

Also provided is method for detecting an analyte in a sample comprising (a) providing a sample in an aqueous liquid carrier, said liquid carrier also comprising (i) a salt or a sugar and (ii) a hygroscopic material; (b) contacting said liquid sample with (i) a reporter agent that binds an analyte in said sample, wherein said reporter agent is labeled with a first color, and (ii) a precipitating particle that binds said analyte, preventing movement of said analyte and any bound capture particles to the droplet center, wherein said precipitating particle is labeled with a second color; (c) placing a droplet of said liquid sample in step (b) on a non-permeable substrate, wherein the thermal conductivity of the substrate is less than 2 times that of the liquid sample; (d) incubating said substrate under conditions promoting inward Marangoni flow in said drop; and (e) detecting said second color at said droplet center when said analyte is present, or detecting a combination of said first and second colors at said droplet center when said analyte is not present. The capture agent may be an analyte binding molecule, or a particle having such an analyte binding molecule disposed thereon.

In yet another embodiment, there is provided a method for detecting an analyte in a sample comprising (a) providing a sample in an aqueous liquid carrier, said liquid carrier also comprising (i) a salt or a sugar and (ii) a hygroscopic material; (b) contacting said liquid sample with (i) capture particles that bind an analyte in said sample, wherein said capture particles are labeled with a first color, (ii) a control reaction particle labeled with a second color, and (iii) a precipitating particle that binds said analyte, preventing movement of said analyte and any bound capture particles to the droplet center; (c) placing a droplet of said liquid sample in step (b) on a non-permeable substrate, wherein the thermal conductivity of the substrate is less than 2 times that of the liquid sample; (d) incubating said substrate under conditions promoting inward Marangoni flow in said drop; and (e) detecting said second color at said droplet center when said analyte is present, or detecting a combination of said first and second colors at said droplet center when said analyte is not present. The precipitating particle may be magnetic, and step (d) may further comprise applying a magnetic field perpendicular to and below said non-permeable substrate. Steps (b) and (c) may be reversed in order. The method may further comprising quantitating said capture particles at said droplet center.

The first and second colors may be yellow and blue or blue and yellow, respectively, and said combination of said first and second colors may be green; or said first and second colors may be red and blue or blue and red, respectively, and said combination of said first and second colors may be purple; or said first and second colors may be yellow and red or red and yellow, respectively, and said combination of said first and second colors may be orange. The capture particles may be located on said non-permeable substrate, and steps (b) and (c) are comprised in a single step of dropping said sample onto said non-permeable substrate. Multiple droplets may be placed on said substrate.

In still yet another embodiment, there is provided a method for detecting an analyte in a sample comprising (a) mixing a sample with capture particles that bind an analyte in said sample; (b) contacting said sample with an aqueous liquid carrier also comprising (i) a salt or a sugar (ii) and a hygroscopic material/surfactant; (c) placing a droplet of said liquid sample in step (b) on a non-permeable substrate, wherein the thermal conductivity of the substrate is less than 2 times that of the liquid sample; and (d) incubating said substrate under conditions promoting inward Marangoni flow in said drop, wherein the presence of capture particles at said droplet center, as compared to a control assay lacking said analyte, reflects the presence of analyte in said sample.

In a further embodiment, there is provided a method for detecting an analyte in a sample comprising (a) providing a sample receptacle containing (i) a capture particles that bind an analyte in said sample, (ii) a salt or a sugar and (iii) a hygroscopic material/surfactant; (b) disposing a sample into said sample receptacle; (c) placing a droplet of said liquid sample in step (b) on a non-permeable substrate, wherein the thermal conductivity of the substrate is less than 2 times that of the liquid sample; and (d) incubating said substrate under conditions promoting inward Marangoni flow in said drop, wherein the presence of capture particles at said droplet center, as compared to a control assay lacking said analyte, reflects the presence of analyte in said sample. The sample receptacle may be a sample collection device. The capture particles, said salt or sugar and said hygroscopic material/surfactant of step (a) may be lyophilized. The capture particles may be magnetic and may be transported to the substrate via magnetic transfer.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects and features of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIGS. 1A-B. (FIG. 1A) A non-uniform evaporation rate along the drop surface combined with a low thermally conductive substrate causes temperature (T) and surface tension (Y) gradients that drive Marangoni flow, (FIG. 1B) A 3-D rendered drawing of the cross-sectional Marangoni flow in FIG. 1A shows radial symmetry around the drop center.

FIGS. 2A-C. Schematic of the assay. (FIG. 2A) A sample is mixed with a solution containing 1 μm-diameter particles that are surface-functionalized with αM13 antibody. Particles remain disperse in the absence of M13 bacteriophage (left), and aggregate in the presence of M13 bacteriophage (right); (FIG. 2B) A 1 μL drop of the reacted solution is deposited on a PDMS substrate. Unaggregated particles are transported to the drop edge by the Maranogni flow fields while large aggregates settle to the bottom and become concentrated in the center of the drop; (FIG. 2C) The final deposition pattern of a negative test shows little-to-no aggregates in the center (left) while a positive test shows an accumulation of aggregates in the center (right).

FIGS. 3A-B. Time-lapse OCT composites taken through the diameter of an evaporating drop at seven different times during drop evaporation. The time sequence shows the accumulation of aggregates at the bottom center of a drop containing $10^6$ αM13-functionalized particles reacted with 0 pM M13 target (FIG. 3A) or 100 pM of M13 target (FIG. 3B). Each of the composite images consists of 200 consecutive OCT frames acquired at 5 fps.

(FIG. 5A) Signal was measured as a function of M13 target concentration by measuring the area of aggregates in the center of the drop using a predefined region of interest having a diameter=0.6 times the mean drop diameter. Signal was normalized for drop volume and divided by the mean 0 pM value to generate a signal-to-noise ratio. Mean values for all M13 target concentrations are plotted (log-linear) for n=15+/−1σ. (FIG. 5B) Signal-to-noise at the low M13 target concentrations are plotted (linear) for n=15+/−1σ. (FIG. 5C) Signal-to-noise, normalized to the maximum value for each of three drops containing 28 pM of M13 target evaporated on a PDMS substrate, is plotted as a function of drop evaporation time. (FIG. 5D) Images of particle residue patterns produced by evaporating a drop of αM13-functionalized particles containing 28 pM of M13 target on a PDMS substrate (left) versus a glass substrate coated with indium tin oxide (ITO, right).

DETAILED DESCRIPTION OF THE INVENTION

I. Drop-Based Principles

Figure 4:
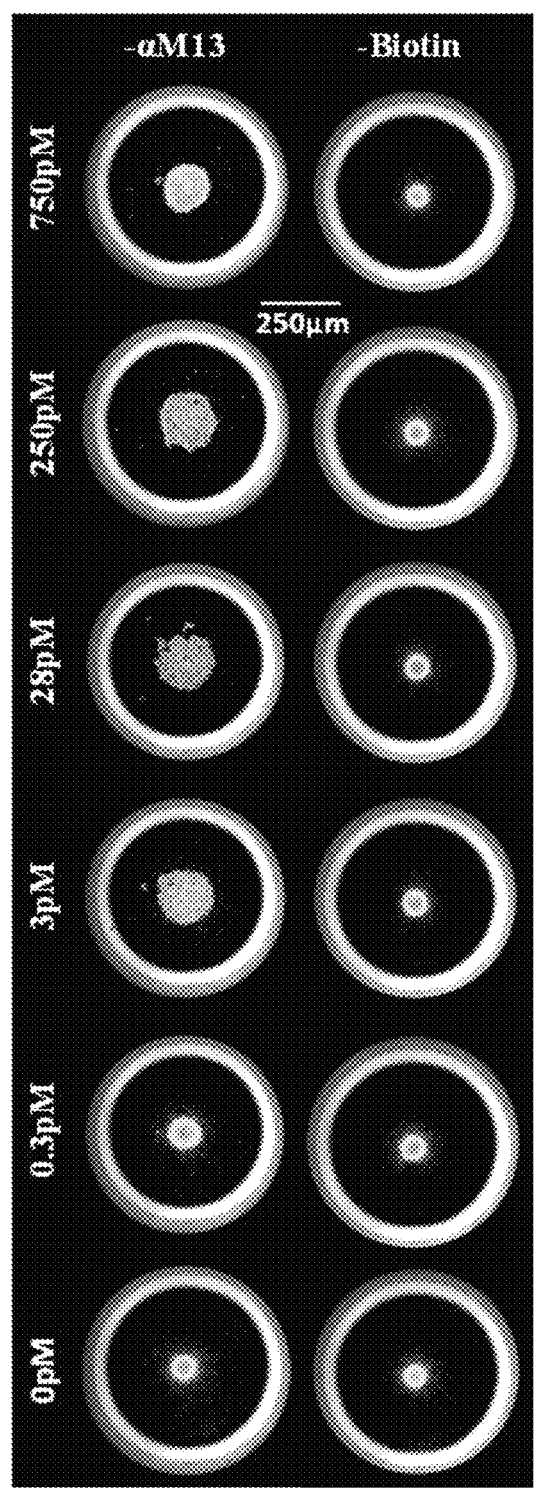
FIG. 4. Change in particle deposition patterns produced by a decrease in M13 target concentration in 1 μL drops containing $10^6$ αM13 antibody-functionalized particles (left panel) evaporated on a PDMS substrate. The right panel is a negative control using biotin-coated particles in place of particles functionalized with αM13 antibody. Signal in the assay is seen as a large spot in the center of the drop at high concentrations of M13 bacteriophage which decreases in size with less M13 bacteriophage (top to bottom). The biotin control particles produce a signal similar in size to the 0 pM sample at all M13 bacteriophage concentrations.

In designing new diagnostic methods, there would be considerable advantages to an assay that is simple to perform, does not require instrumentation, is inexpensive to manufacture, is stable over a variety of environmental conditions, and can be readily interpreted by an unskilled end-user. The need for new approaches to rapid diagnostics for non-industralized countries continues to be highlighted by medical organizations around the world. Most commercial tests suffer from extreme sensitivity to thermal storage conditions and poor performance at low antigen concentrations.

Here, the inventors describe an assay design based on the secondary flows rather than the primary radial flow to generate an easily detectable signal in an evaporating drop in the presence of the M13K07 bacteriophage, a model target. By relying on these secondary flows rather than the primary radial flow, the design reported here circumvents the limitations of the inventors' previously reported assay. Importantly, this revised assay design contains glycerol, which prevents complete drop evaporation and therefore the detrimental effects of salt crystallization. Moreover, this revised assay design relies on an antibody biorecognition element that can be adapted to detect a variety of protein biomarkers rather than the previously used Ni(II)NTA system that has utility specifically for malaria detection.

The secondary flows in an evaporating drop, often referred to as Marangoni flow, are thought to be caused by a surface temperature gradient and corresponding surface tension gradient known as a Marangoni stress (Barash et al., 2009, Hu & Larson, 2005, Hu & Larson, 2006, Savino et al., 2002 and Still et al, 2012). Fluid flows from regions of low surface tension to high surface tension, which, when superimposed with the temperature gradient, creates symmetrical flow fields through the cross section of the drop (i.e., orthogonal to the substrate). These flows can coexist with the primary radial flow and may be either in the same or opposing direction as the primary radial flow (Ristenpart et al., 2007). The existence of Marangoni flow in evaporating drops has been previously described (Barash et al., 2009, Hu & Larson, 2005, Hu & Larson, 2006, Savino et al., 2002 and Still et al, 2012). The surface tension of water interfaces is known to be highly sensitive to trace amounts of contaminants, and therefore Marangoni flow in water drops is thought to be limited or non-existent (Hu & Larson, 2006 and Still et al, 2012).

Unlike primary radial flow which is predominantly two-dimensional and easily imaged with a microscope, Marangoni flow is three-dimensional and requires high frame rate, cross-sectional imaging. Confocal microscopy has been used to track tracer particles in three-dimensional space in an evaporating drop. However, due to a shallow depth of field, confocal microscopy is not currently capable of imaging an entire cross-sectional slice of a colloidal water drop having a height of 300 μm within a time frame that enables particle tracking during drop evaporation (Bodiguel & Leng 2012 and Bodiguel & Leng 2010). Recently, the inventors and others have used optical coherence tomography (OCT) to track particles in an entire cross section of an evaporating drop (Trantum et al., 2013 and Manukyan et al., 2013). The inventors recently reported that OCT imaging revealed weak Marangoni flow in evaporating water drops containing 1 μm-diameter polystyrene particles (Trantum et al., 2013). Under similar experimental conditions, the inventors show here that the addition of (i) a sugar or salt and (ii) a surfactant (Tween-20), dramatically enhance this Marangoni flow in water drops evaporated on a polydimethylsiloxane (PDMS) substrate. In this report, the inventors use OCT to image this Marangoni flow, which generates signal in the assay by transporting biomarker-induced particle aggregates into the center of the drop.

The biosensor design reported here is an immuno-agglutination assay in which biomarker-induced particle aggregates are concentrated at the center of an evaporating drop by Marangoni flow rather than concentrated at the edge of the drop by the primary radial flow. The limit of detection is improved by approximately $10^6$ times compared to the inventors' previously reported assay design that relied on primary radial flow. Also, the assay presented in this study, unlike this previous design, is functional in the presence of physiologic salinity and does not require alignment of the drop over a magnetic field. These and other aspects of the invention described in greater detail below.

II. Assay Reagents

The present invention relies, in one aspect, on the use of a capture particle. The only requirements for the capture particle are that it (a) it is able to bind to an analyte in solution in a selective or specific fashion, and (b) that it will be subject to the fluid dynamics of a surface drop, as described by Deegan et al. (1997). Thus, in one aspect, the particle may be a capture agent, such as an antibody. In other embodiments, particularly for low molecular binding molecules, the capture particle will comprise a scaffold, such as a bead or nanoparticle, and the low molecular binding molecule attached thereto.

Differential evaporation rates resulted in movement within an evaporating drop. Depending on the content of the drop (e.g., salt), and various environmental factors affecting evaporation (e.g., temperature differential), the evaporation will produce primary radial flow or Marangoni flow, resulting in edge ring formation versus center spot formation. Altering these controlling factors to produce one or the other is a primary design consideration in low resource assays relying on drop deposition.

The assay design uses Marangoni flow to concentrate target-induced particle aggregates in the center of an evaporating drop. Unlike the primary radial flow that concentrates colloidal particles at the edge of the drop, the Marangoni flow in the assay reported here travels in the opposite direction and concentrates aggregated particles at the center of a drop forming an easily detectable spot. Design parameters including substrate material and solution components will be optimized to promote this center-directed Marangoni flow. This flow pattern is axisymmetric and directed radially outward along the air liquid interface and radially inward along the substrate.

The surface tension gradient from which Marangoni flow fields arise is thought to be caused by a temperature gradient that arises from cooling affects caused by the non-uniform evaporative flux along the drop surface. Originally described by Deegan, the evaporation rate of a drop is greatest at the contact line due to the proximal location of ambient, unsaturated gas resulting in non-uniform evaporation along the air-liquid interface (Deegan, 2000, Deegan et al. 2000 and Deegan et al., 1997). The extent to which non-uniform evaporative cooling effects result in a temperature gradient along the drop surface is determined in part by the rate of heat transfer from the isothermal substrate to the air-liquid interface (Ristenpart et al., 2007). These heat transfer rates are, in part, a function of both the drop height as well as the thermal conductivities of the substrate and liquid.

Importantly, if the thermal conductivity of the substrate is sufficiently low, then evaporative cooling dominates and causes the lowest temperature to occur at the contact line. Conversely, a highly thermally conductive substrate promotes sufficient heat transfer at the contact line to overcome evaporative cooling effects resulting in the greatest temperature at the drop edge and lowest at the center. These temperature gradients cause surface tension gradients which in turn drive the Marangoni flow. According to Ristenpart et al., the drop is coolest at the contact line if the substrate has a thermal conductivity less than 1.45 times that of the liquid causing fluid to flow in the direction indicated in FIG. 1A (Ristenpart et al., 2007). If the substrate has a thermal conductivity greater than 2 times that of the liquid, the flow direction is reversed. Moreover, these Marangoni flow fields are axisymmetric around the drop center resulting in a toroidal geometry when viewed from above the drop. In the absence of biomarker, particles follow these flow fields and are eventually deposited across the substrate surface, predominately at the drop edge resulting in a ring pattern. In the presence of biomarker, aggregated particles rapidly settle to the substrate and are then transported to the drop center by the Marangoni flow fields resulting in a concentrated spot. Due to non-specific particle binding events, a baseline amount of aggregated particles settle at the drop center in the absence of target biomarker and represents noise in the system.

A. Particles and Beads

The present methods rely on biomarker-induced aggregation of particles or beads, or by cross-linking of a capture agent to a large and/or dense particle in the presence of biomarker. In determining the appropriate particle or bead, a number of factors must be considered. These factors include size, density, ligand attachment strategy, stability, aggregation properties, and visibility to an end-user. The discussion below provides a list of suitable bead/particles that can be used in accordance with the present invention.

Particles.

In certain embodiment, the present invention uses various compositions known generically as "particles." Particles can range in size from nanometers (so called nanoparticles) to those in the 10-100 micron size or larger. Particles are often spherical or round, but irregularly shaped particles are also known and useful in accordance with the present invention.

The particles may be made of glass, polystyrene, latex, metal, quantum dot, polymers, silica, metal oxides, ceramics, or any other substance suitable for binding to nucleic acids, or chemicals or proteins which can then attach to nucleic acids. The particles may be rod-shaped or spherical or disc-shaped, or comprise any other shape. The particles may be spectrally distinct by virtue of having a composition containing dyes or ratios or concentrations of one or more dyes or fluorochromes, or may be distinguishable by barcode or holographic images or other imprinted forms of particle coding.

The particles may be magnetic particles, allowing them to be attracted to the surface of the chamber by application of a magnetic field. Likewise, magnetic particles may be dispersed from the surface of the chamber by removal of the magnetic field. The magnetic particles are preferably paramagnetic or superparamagnetic. Paramagnetic and superparamagnetic particles have negligible magnetism in the absence of a magnetic field, but application of a magnetic field induces alignment of the magnetic domains in the particles, resulting in attraction of the particles to the field source. When the field is removed, the magnetic domains return to a random orientation so there is no interparticle magnetic attraction or repulsion. In the case of superparamagnetism, this return to random orientation of the domains is nearly instantaneous, while paramagnetic materials will retain domain alignment for some period of time after removal of the magnetic field.

Of particular suitability in the present invention are metal particles. The metal may, for example, be comprised of silver, antimony, bismuth, lanthanum, tin, thallium, titanium, cerium, iron, cadmium, chromium, nickel, manganese, cobalt, zinc or gold.

Beads.

Beads are considered to be a particular kind of particle. Such beads include those produced by Luminex (Austin Tex.) or MicroMod (Germany), made of polystyrene, Dyanbeads®, produced by Invitrogen, or nylon beads.

B. Substrates

Flat, non-permeable substrates for deposition of the drop in accordance with the present invention can be made of, or coated with, virtually any type of material that provides the necessary fluid dynamics. Such materials include plastic (e.g., polystyrene) or other material with appropriate high thermal conductivity and high contact angle (hydrophobic). Such surfaces may be derivatized to facilitate the use of different solvent, capture agents and detection methods. Of particular use are plastic slides. Substrates having high thermal conductivity and/or and a high contact angle (hydrophobic) are desired.

C. Analyte Binding Agents

Analyte binding agents in accordance with the present invention include virtually any type of agent that is capable of interacting in a selective or specific manner with a cognate binding partner. Such agents include proteins, chemicals, nucleic acids, metals, or carbohydrates (e.g., lectins). In particular, the protein may be an antibody, a receptor, an antigen, or a fragment of any of the foregoing.

D. Liquid Carriers

Marangoni flow is relatively easy to achieve in evaporating drops of organic solvents, but is more challenging in aqueous solutions, such as the type of liquid used in a bioassay. To promote Marangoni flow in aqueous drops sufficiently strong to create a signal (concentrated spot) in the assay, the certain design parameters are required:

a substrate that has a relatively high thermal conductivity, such as polydimethylsiloxane (PDMS), and a high contact angle (hydrophobic); and at least one of the following additives: glycerol, salt (e.g., NaCl and LiCl), FICOLL® (copolymer of sucrose and epichlorohydrin) or Betaine.

In order for the assay to work well with fluids containing physiologic salinity, a hygroscopic material must be added to the drop solution in order to avoid crystallization at the end of drop evaporation, notably where the sample is a physiologic/biologic sample already containing salt or sugar.

However, it is possible that, in certain scenarios, the hygroscopic material is not required. First, when analyte capture occurs in a sample that contains adequate salt and pH for the reaction to take place, the capture particles can then be transported to the liquid carrier after analyte is captured. The liquid carrier in this case must still have some salt/sugar present to shield non-specific interactions, but the concentration may be low enough that full evaporation of the drop does not cause sufficient crystallization to ruin the assay. In this case, the hygroscopic material is not necessary. For example, NaCl concentrations ≤50 mM should be sufficient to screen non-specific interactions and not cause detrimental crystallization upon full evaporation of a drop. A NaCl concentration of 50 mM would also be sufficient to create the flow patterns in a drop of liquid carrier evaporated on PDMS.

Second, one may be detecting an analyte that does not have a salt requirement for the detection reaction (e.g., non-biological analytes). In this case, a low amount of salt may be included to shield non-specific interactions, but not be high enough to cause sufficient crystallization to ruin the assay. In this case the hygroscopic material may not be needed. If analyte capture occurs in the liquid carrier (i.e., in the drop), then one needs both salt/sugar and a hygroscopic agent (the salt/sugar to maintain the proper conditions for biochemical reactions and a hygroscopic agent to avoid crystallization by preventing complete evaporation). If analyte detection occurs in a sample first, followed by the capture particles being transported to the liquid carrier, then salt/sugar is not necessarily needed (since the analyte binding step has already taken place), so long as a material is present that meets density constraints, e.g., increasing the density of the water by at least 1%, or to 1.01 g/cm$^3$.

E. Salts

In certain embodiments salts are employed. Both NaCl and LiCl are acceptable for use in accordance with the present methods.

III. Assay Formats

The basic concept involves the use of dectable (e.g., visible) changes in the spot formation at the center of an evaporated drop of fluid to diagnose, for example, an infection or cancer in a subject, or to detect environmental pollutants, toxins, illegal drugs, etc., in virtually any sample. In one design, the aggregation and capture of antigens from a drop of patient's blood deposited and dried on a preprepared glass slide will produce a color change at the center of the drop if there is an infection. The essence of this design combines the microfluidic behavior of an evaporating drop with an agglutination assay.

Numerous formats are possible, and the following discussion is merely provided as an exemplary embodiment.

A. One Particle Format

Various one-bead assays are envisioned. Here, the single particle that binds to an analyte will be transported to the center of a drop via Marangoni flow. Detection of the analyte is then effected through one of several various options. First, the aggregation of particles (due to presence of analyte) in solution may result in a color change relative to non-aggregated material. Here, the mere collection of the aggregated species at the center of the drop permits detection of the color change. Second, one may actually perform a secondary detection step at the center of the drop, where the capture particle has merely served to concentrate the analyte in one spot. It also may be useful to incorporate a secondary binding reagent on the flat surface to capture the analyte, and at the same time retain the capture particle which is detected through various different approaches.

In the single particle format, another material must be present in the solution that is capable of pinning the contact line. In the case of a positive test, most particles are concentrated in the center of the spot—in this case there must be something to maintain a pinned contact line so as to maintain Marangoni flow. If the contact line does not remain pinned, then all materials in solution ultimately collapse to the center of the drop as the contact line recedes during evaporation. Glycerol is effective at fulfilling this requirement, but other similar agents will suffice.

In one embodiment, the inventors propose the development of a new rapid diagnostic test for malaria detection that combines the aggregation behavior of ligand-stabilized AuNPs and the deposition behavior of small volume colloidal-containing droplets on PDMS slides. The resulting diagnostic will consist of Ni-NTA-containing ligands coordinated to the surface of 15 nm AuNPs via thiol-Au bonds. The affinity of pJHRP2 towards Ni-NTA results in crosslinking of multiple AuNPs with the enzyme, causing irreversible aggregation. When a small volume of the reaction mixture is then spotted on a Ni-NTA functionalized PDMS slide, the presence of pJHRP2 induces binding of the aggregate to the slide, leaving a distinct purple spot even after extensive washing with a blocking buffer containing imidazole. This diagnostic will maintain many of the advantages of the antibody-containing RDTs, but also provide more stability and reproducibility in harsh environments.

Much like the current RDT strategies, the proposed design targets pJHRP2. Briefly, pJHRP2 is a 67 kDa protein that consists of 34% histidine assembled in multiple repeats of AHH and AHHAAD. It is the primary target for current RDTs because of its high concentration in host serum, blood, and saliva (Chiodini et al., 2007). With its extraordinarily high content of histidine, pJHRP2 binds selectively to $Ni^{2+}$ and Zn-NTA agarose affinity columns with higher affinity than other enzymes found in blood or serum, including human serum albumin, transferrin, α2-macroglobulin, and histidine-rich glycoprotein (HRG) (Panton et al., 1989; Ghimire et al., 2003). Recent studies have also shown that histidine-tagged proteins bind to NTA ligands functionalized onto gold (Barton et al., 2006; Brinas et al., 2008; De et al., 2009; Hainfield et al., 1999; Lee et al., 2009), polystyrene microspheres (Lauer & Nolan, 2002), and quantum dots (Gupta et al., 2008). The inventors propose that this high binding affinity can be replicated for pJHRP2 with NTA-functionalized gold nanoparticles (NTA AuNPs).

B. Two Particle Format

Two-particle systems can be employed. In this format, each particle would have a different color with one binding biomarker and the other, for example, being a control. In this case the proposed design could be colorimetric, with each bead exhibiting a distinct color.

C. Labels

Luminescent Labels.

Chemical luminescent lables include luminol and cyalume, both of which are activted by hydrogen peroxide. Bioluminescent labels include firefly luciferase, Renilla luciferase, and bacterial luciferase.

Fluorescent Labels.

Fluorescent labels and dyes contemplated for use as conjugates include ALEXA FLUOR® 350, ALEXA FLUOR® 430, AMCA, BODIPY® 630/650, BODIPY® 650/665, BODIPY®-FL, BODIPY®-R6G, BODIPY®-TMR, BODIPY®-TRX, CASCADE BLUE®, CY3 DIRECT®, CY5 DIRECT®, 6-FAM, Fluorescein Isothiocyanate, HEX, 6-JOE, OREGON GREEN® 488, OREGON GREEN® 500, OREGON GREEN® 514, PACIFIC BLUE™, REG, Rhodamine Green, Rhodamine Red, Renographin, ROX, TAMRA, TET, Tetramethylrhodamine, and/or TEXAS RED®.

*Aequorea victoria* are brightly luminescent jellyfish, with glowing points around the margin of the umbrella. Light arises from yellow tissue masses that each consist of about 6000-7000 photogenic cells. The cytoplasm of these cells is densely packed with fine granules that contain a Ca++ activated photoprotein, aequorin, that emits blue-green light, and an accessory green fluorescent protein (GFP), which accepts energy from aequorin and re-emits it as green light. GFP is an extremely stable protein of 238 amino acids, stable in neutral buffers up to 65° C., and displaying a broad range of pH stability from 5.5 to 12. The protein is intensely fluorescent, with a quantum efficiency of approximately 80% and molar extinction coefficient of $2.2 \times 10^4$ cm-1 M-1 (after correction for the known molecular weight). GFP fluoresces maximally when excited at 400 nm with a lesser peak at 475 nm, and fluorescence emission peaks at 509 nm. Since the purification and cloning of the GFP from *Aequorea Victoria*, similar fluorescent proteins have been isolated and cloned from many other species including dynoflagelates, sea pens, and reef corals.

Two variants of the *Aequorea victoria* GFP, cyan fluorescent protein (CFP) and yellow fluorescent protein (YFP), have special fluorescence excitation and emission properties that are well suited to measurement of close molecular distances. Thus, variants of this type have been the most widely used for FRET experiments. When these two molecules are positioned at distances closer than 7 nm of each other, energy transfer can occur from the excited state of the donor molecule (CFP), to the unoccupied excited state of the acceptor molecule (YFP) by a process commonly referred to as fluorescence (or Förster) resonance energy transfer (FRET). FRET between CFP and YFP can be detected using a wide variety of spectroscopic and fluorescence microscopy techniques and is often used to report protein-protein interactions or changes in the conformation state of a peptide or protein. Since the efficiency of FRET is directly related to the spectroscopic properties of both the donor and acceptor molecules, improvements can be made to the fluorescence properties of the fluorophores, such as to increase both the FRET efficiency and the chances of successful detection. FRET has also been used to quantify association of a protein of interest with an organelle (Chiu et al., 2002). As more fluorescent proteins are developed, other FRET pairs are being tried, such as the CFP to an Orange FP from reef coral, called mKO (Karasawa et al., 2004). One of the strengths of the present invention is that it is broadly applicable to any pair of fluorescent proteins that have spectral properties sufficient to generate FRET.

The gene of the green fluorescent protein has been isolated and its sequence has also been determined (Prasher et al., 1992). There have also been numerous reports of amino acid sequences of other fluorescent proteins or their mutants, for example, as described in Tsein (1998) and the literature cited therein. Fluorescent proteins include green fluorescent protein, red fluorescent protein, yellow fluorescent protein, GFP, BFP, CFP, YFP, EGFP, EYFP, Venus, Citrine, phiYFP, copGFP CGFP, ECFP, Cerulean, CyPet, T-Sapphire, Emerald, YPet, AcGFP1, AmCyan, AsRed2, dsRed, dsRed2, dsRed-Express, EBFP, HcRed, ZsGreen, ZsYellow, J-Red, TurboGFP, Kusabira Orange, Midoriishi Cyan, mOrange, DsRed-monomer, mStrawberry, mRFP1, tdTomato, mCherry, mPlum, and mRaspberry.

The term "cyan fluorescent protein (CFP)" as used herein is defined as any fluorescent protein with an absorption maximum between 420 and 460 nm, and a fluorescence maximum between 460 and 500 nm. These proteins have mainly been derived from the wild-type *Aequoria* GFP with a Y66W mutation, resulting in a primary excitation peak at ~434 nm with minor excitation maxima at ~452 nm, and a primary emission peak is 477 nm with minor shoulder at ~505 nm (Heim et al., 1994). Other fluorescent proteins are termed "green fluorescent protein (GFP)", meaning proteins with absorption maxima between 480 and 500 nm and fluorescence maxima between 500 and 515 nm, and "yellow fluorescent protein (YFP)" meaning proteins with absorption maxima between 500 and 520 nm and fluorescence maxima between 515 and 535 nm.

Colorimetric Labels.

o-Phenylenediamine, ABTS and pNPP are all colorimetric substrates for hydrogen peroxidase.

Enzyme Labels.

Examples of suitable enzymes include urease, alkaline phosphatase, (horseradish) hydrogen peroxidase or glucose oxidase.

Radiolabels.

Radioactive isotopes for diagnostic application include astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$.

D. Detection Methods

One of the central advantages of the present invention is the use of simple and inexpensive detection methods that do not require sophisticated equipment or trained personnel. However, the present assays also are amenable to such more sophisticated procedures, which are specifically contemplated to be included herein.

Visual.

Perhaps the most straightforward detection method is visible. Visible detection may rely on a color (presence or absence), color change, luminescence, or fluorescence. The present invention contemplates that the spot-like product produced from drop evaporation will provide a readily recongizable feature that permits home and field use of the assays with minimal instruction (i.e., package inserts with instructions and diagrams).

Light Microscopy.

Light or optical microscopy involves passing visible light transmitted through or reflected from the sample through a single or multiple lenses to allow a magnified view of the sample. The resulting image can be detected directly by the eye, imaged on a photographic plate or captured digitally. The single lens with its attachments, or the system of lenses and imaging equipment, along with the appropriate lighting equipment, sample stage and support, makes up the basic light microscope. The most recent development is the digital microscope which uses a CCD camera to focus on the exhibit of interest. The image is shown on a computer screen since the camera is attached to it via a USB port, so eye-pieces are unnecessary.

Bright field microscopy is the simplest of all the light microscopy techniques. Sample illumination is via transmitted white light, i.e., illuminated from below and observed from above. Limitations include low contrast of most biological samples and low apparent resolution due to the blur of out of focus material. The simplicity of the technique and the minimal sample preparation required are significant advantages.

The use of oblique (from the side) illumination gives the image a 3-dimensional appearance and can highlight otherwise invisible features. A more recent technique based on this method is Hoffmann's modulation contrast, a system found on inverted microscopes for use in cell culture. Oblique illumination suffers from the same limitations as bright field microscopy (low contrast of many biological samples; low apparent resolution due to out of focus objects), but may highlight otherwise invisible structures.

Dark field microscopy is a technique for improving the contrast of unstained, transparent specimens. Dark field illumination uses a carefully aligned light source to minimize the quantity of directly-transmitted (unscattered) light entering the image plane, collecting only the light scattered by the sample. Darkfield can dramatically improve image contrast—especially of transparent objects—while requiring little equipment setup or sample preparation. However, the technique does suffer from low light intensity in final image of many biological samples, and continues to be affected by low apparent resolution.

Rheinberg illumination is a special variant of dark field illumination in which transparent, colored filters are inserted just before the condenser so that light rays at high aperture are differently colored than those at low aperture (i.e., the background to the specimen may be blue while the object appears self-luminous yellow). Other color combinations are possible but their effectiveness is quite variable.

Dispersion staining is an optical technique that results in a colored image of a colorless object. This is an optical staining technique and requires no stains or dyes to produce a color effect. There are five different microscope configurations used in the broader technique of dispersion staining They include brightfield, Beck' line, oblique, darkfield, phase contrast, and objective stop dispersion staining When certain compounds are illuminated with high energy light, they then emit light of a different, lower frequency. This effect is known as fluorescence. Often specimens show their own characteristic autofluorescence image, based on their chemical makeup.

This method is of critical importance in the modern life sciences, as it can be extremely sensitive, allowing the detection of single molecules. Many different fluorescent dyes can be used to stain different structures or chemical compounds. One particularly powerful method is the combination of antibodies coupled to a fluorochrome as in immunostaining Examples of commonly used fluorochromes are fluorescein or rhodamine. The antibodies can be made tailored specifically for a chemical compound. For example, one strategy often in use is the artificial production of proteins, based on the genetic code (DNA). These proteins can then be used to immunize rabbits, which then form antibodies which bind to the protein. The antibodies are then coupled chemically to a fluorochrome and then used to trace the proteins in the cells under study.

Highly-efficient fluorescent proteins such as the green fluorescent protein (GFP) have been developed using the molecular biology technique of gene fusion, a process which links the expression of the fluorescent compound to that of the target protein. This combined fluorescent protein is generally non-toxic to the organism and rarely interferes with the function of the protein under study. Genetically modified cells or organisms directly express the fluorescently-tagged proteins, which enables the study of the function of the original protein in vivo.

Since fluorescence emission differs in wavelength (color) from the excitation light, a fluorescent image ideally only shows the structure of interest that was labeled with the fluorescent dye. This high specificity led to the widespread use of fluorescence light microscopy in biomedical research. Different fluorescent dyes can be used to stain different biological structures, which can then be detected simultaneously, while still being specific due to the individual color of the dye. To block the excitation light from reaching the observer or the detector, filter sets of high quality are needed. These typically consist of an excitation filter selecting the range of excitation wavelengths, a dichroic mirror, and an emission filter blocking the excitation light. Most fluorescence microscopes are operated in the Epi-illumination mode (illumination and detection from one side of the sample) to further decrease the amount of excitation light entering the detector.

Fluorescence microscopy is extremely powerful due to its ability to show specifically labeled structures within a complex environment and also because of its inherent ability to provide three-dimensional information on biological structures. Unfortunately, this information is blurred by the fact that upon illumination all fluorescently labeled structures emit light no matter if they are in focus or not. This means that an image of a certain structure is always blurred by the contribution of light from structures which are out of focus. This phenomenon becomes apparent as a loss of contrast especially when using objectives with a high resolving power, typically oil immersion objectives with a high numerical aperture.

Fortunately though, this phenomenon is not caused by random processes such as light scattering but can be relatively well defined by the optical properties of the image formation in the microscope imaging system. If one considers a small fluorescent light source (essentially a bright spot), light coming from this spot spreads out the further out of focus one is. Under ideal conditions this produces a sort of "hourglass" shape of this point source in the third (axial) dimension. This shape is called the point spread function (PSF) of the microscope imaging system. Since any fluorescence image is made up of a large number of such small fluorescent light sources the image is said to be "convolved by the point spread function."

Knowing this point spread function means that it is possible to reverse this process to a certain extent by computer based methods commonly known as deconvolution microscopy. There are various algorithms available for 2D or 3D deconvolution. They can be roughly classified in non-restorative and restorative methods. While the non restorative methods can improve contrast by removing out of focus light from focal planes, only the restorative methods can actually reassign light to it proper place of origin. This can be an advantage over other types of 3D microscopy such as confocal microscopy, because light is not thrown away but reused. For 3D deconvolution one typically provides a series of images derived from different focal planes (called a Z-stack) plus the knowledge of the PSF which can be either derived experimentally or theoretically from knowing all contributing parameters of the microscope.

Automated Detection. A variety of automated devices for reading colorimetric, fluorescent and chemilluminescent reactions are available from commercial sources. The machines, often used for reading of large throughput assays using multi-well plates, can be adapted for use with the assays of the present invention. The output may advantageously be transferred to a computer for further analysis and manipulation. In particular, one detection embodiment involves spotting of the material onto a cell phone camera lens, or on a platform (e.g., disposable) that can be affixed adjacent to the camera lens. Then, simply by taking a picture, one can obtain a digital image of the material which optionally may be analyzed by (a) emailing the image to a computer with image processing software, or (b) image processing software loaded onto the cell phone itself.

FRET. Förster Resonance Energy Transfer (FRET) is a phenomenon in which the excited-state energy in one molecule (called the donor) is transferred to another molecule by a radiationless coupling. This mechanism was first correctly described by Förster, and differs from other types of energy transfer, such as electron sharing (Dexter) or trivial transfer (emission of a photon from the donor and reabsorption by the acceptor). The Dexter mechanism requires the two molecules to be in physical contact, while trivial transfer is a very low probability. In contrast, the Förster mechanism exhibits a high probability when the two molecules are within the Förster radius, which is defined for any given pair of fluorophores.

The overall FRET efficiency depends on the Förster radius, and is determined by several factors and is directly related to the amount of overlap between the absorption spectra of the acceptor molecule and the emission spectra of the donor molecule. The amount of FRET also depends on the alignment of the donor and acceptor molecules, although most biological systems are not rigidly aligned. The FRET efficiency is also affected by the ability of the acceptor molecule to absorb light, as indicated by its molar extinction coefficient, and the overall stability of the excited state of the donor molecule, as indicated by the probability that absorption will lead to fluorescence (quantum yield) and the lifetime of the excited state.

FRET between two different fluorophores can be assayed by several methods: looking at the change in color of the fluorescence, measuring the fluorescence lifetime of the donor, examining the changes upon photobleaching either the donor or acceptor, or as the inventors show here: by measuring the fluorescence polarization of the acceptor. Regardless of the approach, most of these assays share common features of the instrumentation.

IV. Samples and Diagnostic Targets

A. Samples

Samples can come from a wide variety of sources. In one aspect, the sample is derived from a living organisms, include a plant, animal (veterinary uses) or human. Such samples may involve solid material such as feces or tissues (including biopsies), tissue extracts, or fluids, including body fluids such as saliva, sputum, tears, blood, serum, plasma, urine, exudate, transudate, spinal fluid, semen or nasal discharge. Such samples may be solubilized or diluted, as needed, to perform the assays of the present invention. Solvents for use in solubilizing or diluting samples include water, acetone, methanol, toluene, ethanol or others.

Other samples, are manufactured, industrial or environmental, and may or may not contain living cells or organisms. Such sample may include soil, water, foodstuffs, alcoholic beverages, building products, bulk chemicals or reagents, including drugs. Again, such samples may be solubilized or diluted, as needed, to perform the assays of the present invention.

B. Targets

Autoimmune Antigens or Antibodies Thereto.

Autoimmune diseases can be generally classified as antibody-mediated, T-cell mediated, or a combination of antibody-mediated and T-cell mediated. Thus, antibodies or T-cell receptors can be identified with specificity to a variety of endogenous antigens. Such auto-antibodies (e.g., antinuclear antibodies) may be implicated in various disease including insulin-dependent (type I) diabetes mellitus, rheumatoid arthritis, multiple sclerosis, systemic lupus erythematosus (SLE), and inflammatory bowel disease (i.e., Crohn's disease and ulcerative colitis). Other autoimmune diseases include, without limitation, alopecia areata, acquired hemophilia, ankylosing spondylitis, antiphospholipid syndrome, autoimmune hepatitis, autoimmune hemolytic anemia, cardiomyopathy, celiac sprue dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, discoid lupus, essential mixed cryoglobulinemia, fibromyalgia, fibromyositis, Guillain-Barr syndrome, idiopathic pulmonary fibrosis, idiopathic thrombocytopenic purpura, IgA nephropathy, juvenile arthritis, lichen planus, myasthenia gravis, polyarteritis nodosa, polychondritis, polyglandular syndromes, dermatomyositis, primary agammaglobulinemia, primary biliary cirrhosis, psoriasis, Raynaud's phenomena, Reiter's syndrome, sarcoidosis, stiff-man syndrome, Takayasu arthritis, temporal arteritis/giant cell arteritis, uveitis, vasculitis, and vitiligo.

In particular autoimmune diseases, antibodies to self antigens are frequently observed. For example for systemic lupus erythematosus autoantibodies have been described to single-stranded and double-stranded DNA or RNA (Vallin et al., 1999; Hoet et al., 1999; yen Venrooij, 1990). The levels of autoantibodies found in the serum of autoimmune patients very often are found to correlate with disease severity. The pattern of autoantibodies that arise, e.g., in human SLE, suggest that intact macromolecular particles, such as RNA- or DNA-containing complexes, could themselves be immunogenic and anti-nucleic acid antibodies could therefore arise (Lotz et al., 1992; Mohan et al., 1993). Such DNA or RNA released from, e.g., apoptotic cells or DNA- or RNA-containing microbes present in serum of autoimmune patients, could be responsible for inflammation that contributes to the autoimmune disease (Fatenejad, 1994; Malmegrim et al., 2002; Newkirk et al., 2001). Indeed CpG-containing sequences could be identified from SLE serum that induces an efficient immune response dominated by IFN-α secretion that is thought to contribute to the development of to autoimmune diseases (Magnusson et al., 2001; Ronnblom et al., 2001). In addition, the epitopes for anti-RNA antibodies could be identified and are composed of G,U-rich sequences (Tsai et al., 1992; Tsai et al., 1993). G,U-rich sequences appear to be natural ligands for TLR7 and TLR8 and, therefore, can mediate immune stimulatory responses that in principle could contribute to autoimmune diseases or the development of autoimmune diseases (PCT/US03/10406).

Specific antigens to which auto-antibodies are produced include β2-glycoprotein, cardiolipin, CCP, CENP, GBM, gliadin, Jo-1, LKM1, La, MPO, Parietal Cell antigens, PR3, Ro, SS-B/La, SS-A/Ro, Sc1-70, Sm, sperm transglutaminase, TPO and U1RNP.

Infectious Agents.

Infections refer to any condition in which there is an abnormal collection or population of viable intracellular or extracellular microbes in a subject. Various types of microbes can cause infection, including microbes that are bacteria, microbes that are viruses, microbes that are fungi, and microbes that are parasites. Detection of antigens or nucleic acids associated with these microbes, or antibodies thereto, is contemplated in accordance with the present invention.

Bacteria include, the 83 or more distinct serotypes of pneumococci, streptococci such as *S. pyogenes, S. agalactiae, S. equi, S. canis, S. bovis, S. equinus, S. anginosus, S. sanguis, S. salivarius, S. mitis, S. mutans*, other viridans streptococci, peptostreptococci, other related species of streptococci, enterococci such as *Enterococcus faecalis, Enterococcus faecium*, staphylococci, such as *Staphylococcus epidermidis, Staphylococcus aureus, Hemophilus influenzae*, pseudomonas species such as *Pseudomonas aeruginosa, Pseudomonas pseudomallei, Pseudomonas mallei*, brucellas such as *Brucella melitensis, Brucella suis, Brucella abortus, Bordetella pertussis, Borellia* species, such as *Borellia burgedorferi Neisseria meningitidis, Neisseria gonorrhoeae, Moraxella catarrhalis, Corynebacterium diphtheriae, Corynebacterium ulcerans, Corynebacterium pseudotuberculosis, Corynebacterium pseudodiphtheriticum, Corynebacterium urealyticum, Corynebacterium hemolyticum, Corynebacterium equi*, etc. *Listeria monocytogenes, Nocordia asteroides, Bacteroides* species, *Actinomycetes* species, *Treponema pallidum, Leptospirosa* species, *Haemophilus* species, *Helicobacter* species, including *Helicobacter pylori, Treponema* species and related organisms. The invention may also be useful against gram negative bacteria such as *Klebsiella pneumoniae, Escherichia coli, Proteus, Serratia* species, *Acinetobacter, Yersinia pestis, Francisella tularensis, Enterobacter* species, *Bacteroides* and *Legionella* species, *Shigella* species, *Mycobacterium* species (e.g., *Mycobacterium tuberculosis, Mycobacterium bovis* or other mycobacteria infections), *Mycobacterium avium* complex (MAC), *Mycobacterium marinum, Mycobacterium fortuitum, Mycobacterium kansaii, Yersinia* infections (e.g., *Yersinia pestis, Yersinia enterocolitica* or *Yersinia pseudotuberculosis*) and the like.

In addition, the invention contemplates detection of parastic organisms such as *Cryptosporidium, Entamoeba, Plasmodium* spp., such as *Plasmodium falciparum, Plasmodium malariae, Plasmodium ovale*, and *Plasmodium vivax* and *Toxoplasma gondii, Giardia, Leishmania, Trypanasoma, Trichomonas, Naegleria, Isospora belli, Trichomonas vaginalis, Wunchereria, Ascaris, Schistosoma* species, *Cyclospora* species, for example, and for *Chlamydia trachomatis* and other *Chlamydia* infections such as *Chlamydia psittaci*, or *Chlamydia pneumoniae*, for example. Of course it is understood that the invention may be used on any pathogen against which an effective antibody can be made.

Fungal and other mycotic pathogens (some of which are described in Human Mycoses (1979; Opportunistic Mycoses of Man and Other Animals (1989); and Scrip's Antifungal Report (1992), are also contemplated as a target of diagnosis. Fungi disease contemplated in the context of the invention include, but are not limited to, Aspergillosis, Black piedra, Candidiasis, Chromomycosis, Cryptococcosis, Onychomycosis, or Otitis externa (otomycosis), Phaeohyphomycosis, Phycomycosis, Pityriasis versicolor, ringworm, Tinea barbae, Tinea capitis, Tinea corporis, Tinea cruris, Tinea favosa, Tinea imbricata, Tinea manuum, Tinea nigra (palmaris), Tinea pedis, Tinea unguium, Torulopsosis, Trichomycosis *axillaris*, White *piedra*, and their synonyms, to severe systemic or opportunistic infections, such as, but not limited to, Actinomycosis, Aspergillosis, Candidiasis, Chromomycosis, Coccidioidomycosis, Cryptococcosis, Entomophthoramycosis, Geotrichosis, Histoplasmosis, Mucormycosis, Mycetoma, Nocardiosis, North American Blastomycosis, Paracoccidioidomycosis, Phaeohyphomycosis, Phycomycosis, pneumocystic pneumonia, Pythiosis, Sporotrichosis, and Torulopsosis, and their synonyms, some of which may be fatal. Known fungal and mycotic pathogens include, but are not limited to, Absidia spp., Actinomadura madurae, *Actinomyces* spp., *Allescheria boydii, Alternaria* spp., *Anthopsis deltoidea, Apophysomyces elegans, Arnium leoporinum, Aspergillus* spp., *Aureobasidium pullulans, Basidiobolus ranarum, Bipolaris* spp., *Blastomyces dermatitidis, Candida* spp., *Cephalosporium* spp., *Chaetoconidium* spp., *Chaetomium* spp., *Cladosporium* spp., *Coccidioides immitis, Conidiobolus* spp., *Corynebacterium tenuis, Cryptococcus* spp., *Cunninghamella bertholletiae, Curvularia* spp., *Dactylaria* spp., *Epidermophyton* spp., *Epidermophyton floccosum, Exserophilum* spp., *Exophiala* spp., *Fonsecaea* spp., *Fusarium* spp., *Geotrichum* spp., *Helminthosporium* spp., *Histoplasma* spp., *Lecythophora* spp., *Madurella* spp., *Malassezia furfur, Microsporum* spp., *Mucor* spp., *Mycocentrospora acerina, Nocardia* spp., *Paracoccidioides brasiliensis, Penicillium* spp., *Phaeosclera Dematioides, Phaeoannellomyces* spp., *Phialemonium obovatum, Phialophora* spp., *Phoma* spp., *Piedraia hortai, Pneumocystis carinii, Pythium insidiosum, Rhinocladiella aquaspersa, Rhizomucor pusillus, Rhizopus* spp., *Saksenaea vasiformis, Sarcinomyces phaeomuriformis, Sporothrix schenckii, Syncephalastrum racemosum, Taeniolella boppii, Torulopsosis* spp., *Trichophyton* spp., *Trichosporon* spp., *Ulocladium chartarum, Wangiella dermatitidis, Xylohypha* spp., *Zygomyetes* spp. and their synonyms. Other fungi that have pathogenic potential include, but are not limited to, *Thermomucor indicae-seudaticae, Radiomyces* spp., and other species of known pathogenic genera.

Examples of viruses that have been found in humans include but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunga viruses, phleboviruses and Nairo viruses); Arenaviridae (hemorrhagic fever viruses); Reoviridae (e.g., reoviruses, orbiviurses and rotaviruses); Bornaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g., African swine fever virus); unclassified viruses (e.g., the agent of delta hepatitis (thought to be a defective satellite of hepatitis B virus), Hepatitis C; Norwalk and related viruses, and astroviruses); and resipiratory syncytial virus (RSV).

Other medically relevant microorganisms have been described extensively in the literature, e.g., see Medical Microbiology (1983), the entire contents of which is hereby incorporated by reference.

Cancer Antigens.

Many human cancers express cell surface molecule that are specific to the cancer cell, i.e., they are not expressed or expressed in greatly reduced quantity by normal human somatic cells. The role of these antigens in cancerogenesis and cancer progression is often poorly understood, however, independent of their biological functions these antigens are attractive antibody targets for diagnostic applications. Such tumor markers include alpha-feto protein, beta-2-microglobulin, bladder tumor antigen, CA 15-3, CA 19-9, CA 72-4, CA-125, calcitonin, carcinoembryonic antigen, epidermal growth factor receptor, estrogen receptor, human chorionic gonadotropin, Her-2/neu, neuron-specific *enolase*, NPM22, progesterone receptor, prostate specific antigen, prostate-specific membrane antigen, prostatic acid phosphatase, S-100, TA-90 and thyroglobulin.

Toxins, Metals and Chemicals.

A particular type of chemical or biological agent is a toxin. Toxins can be biological, i.e., produced by an organism. These include toxins that may be used in biological warfare or terrorism, including ricin, anthrax toxin, and botulism toxin. Other toxins are pesticides (insecticides, herbicides; e.g., organophosphates), industrial contaminants (heavy metals, such as cadmium, thallium, copper, zinc, selenium, antimony, nickel, chromium, arsenic, mercury or lead; complex hydrocarbons, include PCBs, and petroleum byproducts; asbestos), and chemical warfare reagents (sarin, soman, cyclosarin, VX, VG, GV, phosgene oxime, nitrogen mustard, sulfur mustard and cyanogen chloride). Table 1 below shows a further list of toxic industrial chemicals (TICs). A specific list of 12 banned persistant organic pollutants includes PCBs, DDT, dioxins, chlordane, furans, hexochlorobenzene, aldrin, mirex, dieldrin, toxaphene, endrin, and heptachlor.

TABLE 1

TICs listed by hazard index

| High | Medium | Low |
|---|---|---|
| Ammonia (CAS# 7664-41-7) | Acetone cyanohydrin (CAS# 75-86-5) | Allyl isothiocyanate (CAS# 57-06-7) |
| Arsine (CAS# 7784-42-1) | Acrolein (CAS# 107-02-8) | Arsenic trichloride (CAS# 7784-34-1) |

TABLE 1-continued

TICs listed by hazard index

| High | Medium | Low |
|---|---|---|
| Boron trichloride (CAS#10294-34-5) | Acrylonitrile (CAS# 107-13-1) | Bromine (CAS# 7726-95-6) |
| Boron trifluoride (CAS#7637-07-2) | Allyl alcohol (CAS# 107-18-6) | Bromine chloride (CAS# 13863-41-7) |
| Carbon disulfide (CAS# 75-15-0) | Allylamine (CAS# 107-11-9) | Bromine pentafluoride (CAS# 7789-30-2) |
| Chlorine (CAS# 7782-50-5) | Allyl chlorocarbonate (CAS# 2937-50-0) | Bromine trifluoride (CAS# 7787-71-5) |
| Diborane (CAS# 19287-45-7) | Boron tribromide (CAS# 10294-33-4) | Carbonyl fluoride (CAS# 353-50-4) |
| Ethylene oxide (CAS# 75-21-8) | Carbon monoxide (CAS# 630-08-0) | Chlorine pentafluoride (CAS# 13637-63-3) |
| Fluorine (CAS# 7782-41-4) | Carbonyl sulfide (CAS# 463-58-1) | Chlorine trifluoride (CAS# 7790-91-2) |
| Formaldehyde (CAS# 50-00-0) | Chloroacetone (CAS# 78-95-5) | Chloroacetaldehyde (CAS# 107-20-0) |
| Hydrogen bromide (CAS# 10035-10-6) | Chloroacetonitrile (CAS# 7790-94-5) | Chloroacetyl chloride (CAS# 79-04-9) |
| Hydrogen chloride (CAS# 7647-01-0) | Chlorosulfonic acid (CAS# 7790-94-5) | Crotonaldehyde (CAS# 123-73-9) |
| Hydrogen cyanide (CAS#74-90-8) | Diketene (CAS# 674-82-8) | Cyanogen chloride (CAS# 506-77-4) |
| Hydrogen fluoride (CAS# 7664-39-3) | 1,2-Dimethylhydrazine (CAS# 540-73-8) | Dimethyl sulfate (CAS# 77-78-1) |
| Hydrogen sulfide (CAS# 7783-0604) | Ethylene dibromide (CAS# 106-93-4) | Diphenylmethane-4,4'-diisocyanate (CAS# 101-68-8) |
| Nitric acid, fuming (CAS# 7697-37-2) | Hydrogen selenide (CAS# 7783-07-5) | Ethyl chlroroformate (CAS# 541-41-3) |
| Phosgene (CAS# 75-44-5) | Methanesulfonyl chloride (CAS# 124-63-0) | Ethyl chlorothioformate (CAS# 2941-64-2) |
| Phosphorus trichloride (CAS# 7719-12-2) | Methyl bromide (CAS# 74-83-9) | Ethyl phosphonothioic dichloride (CAS# 993-43-1) |
| Sulfur dioxide (CAS# 7446-09-5) | Methyl chloroformate (CAS# 79-22-1) | Ethyl phosphonic dichloride (CAS# 1066-50-8) |
| Sulfuric acid (CAS# 7664-93-9) | Methyl chlorosilane (CAS# 993-00-0) | Ethyleneimine (CAS# 151-56-4) |
| Tungsten hexafluoride (CAS# 7783-82-6) | Methyl hydrazine (CAS# 60-34-4) | Hexachlorocyclopentadiene (CAS# 77-47-4) |
|  | Methyl isocyanate (CAS# 624-83-9) | Hydrogen iodide (CAS# 10034-85-2) |
|  | Methyl mercaptan (CAS# 74-93-1) | Iron pentacarbonyl (CAS# 13463-40-6) |
|  | Nitrogen dioxide (CAS# 10102-44-0) | Isobutyl chloroformate (CAS# 543-27-1) |
|  | Phosphine (CAS# 7803-51-2) | Isopropyl chloroformate (CAS# 108-23-6) |
|  | Phosphorus oxychloride (CAS# 10025-87-3) | Isopropyl isocyanate (CAS# 1795-48-8) |
|  | Phosphorus pentafluoride (CAS# 7647-19-0) | n-Butyl chloroformate (CAS# 592-34-7) |
|  | Selenium hexafluoride (CAS# 7783-79-1) | n-Butyl isocyanate (CAS# 111-36-4) |
|  | Silicon tetrafluoride (CAS# 7783-61-1) | Nitric oxide (CAS# 10102-43-9) |
|  | Stibine (CAS# 7803-52-3) | n-Propyl chloroformate (CAS# 109-61-5) |
|  | Sulfur trioxide (CAS# 7446-11-9) | Parathion (CAS#: 56-38-2) |
|  | Sulfuryl fluoride (CAS# 2699-79-8) | Perchloromethyl mercaptan (CAS# 594-42-3) |
|  | Tellurium hexafluoride (CAS# 7783-80-4) | sec-Butyl chloroformate (CAS# 17462-58-7) |
|  | n-Octyl mercaptan (CAS# 111-88-6) | tert-Butyl isocyanate (CAS# 1609-86-5) |
|  | Titanium tetrachloride (CAS# 7550-45-0) | Tetraethyl lead (CAS# 78-00-2) |
|  | Tricholoroacetyl chloride (CAS# 76-02-8) | Tetraethyl pyrophosphate (CAS# 107-49-3) |
|  | Trifluoroacetyl chloride (CAS# 354-32-5) | Tetramethyl lead (CAS# 75-74-1) |
|  |  | Toluene 2,4-diisocyanate (CAS# 584-84-9) |
|  |  | Toluene 2,6-diisocyanate (CAS# 91-08-7) |

Plant Products.

In certain embodiments, the present invention will allow one to assess the content of plant materials. For example, one can measure the health of a plant by measuring the nutrient content of the plants' leaves. One can also make decisions about harvesting of crops by assessing the content of fruit or vegetable tissue. For example, in wine-making, the sugar content of grapes is an important factor in determining harvest time. Also, when selecting crops for breeding, identifying plants with various desirable traits (nutrient content, expression of endogenous products or transgenes) is critical.

Drugs.

In another aspect of the invention, the assays may be used to detect or measure drugs in samples. The drugs may be therapeutic agents, and the assay is designed to assess drug levels in the subject with the goal of optimizing dosage. Alternatively, illicit drugs may be detected, and include alcohol, amphetamines, methamphetamine, MDMA, barbiturates, phenobarbitol, benzodiazepines, cannabis, cocaine, codeine, morphine, cotinine, heroin, LSD, methadone, PCP, or licit drugs banned for particular purposes, such as sporting events, including anabolic steroids, hormones (EPO, hGH, IGF-1, hCG, insulin, corticotrophins), β2 agonists, anti-estrogens, diuretics, stimulants, and glucocorticosteroids.

Lipids.

Lipids are biologically relevant targets for assays of the present invention. For example, the ability to detect and quantitate lipids in the blood can serve to assess risk of atherosclerotic disease, as well as to monitor the efficacy of therapy therefore. Thus, LDL, HDL and triglyceride measurements are of use.

Sugars.

While assessing sugar levels may be of general medical interest, sugars are particularly relevant to diabetes management and therapy. Other sugars of relevance include those produced by bacteria and fungi in biofilm formation, and those produced during food or beverage production.

V. Kits

In accordance with the present invention, various reagents may be packaged in the form of a kit. The kit may comprise suitably aliquoted particles/beads in derivatized or underivatized form, and may also include reagents for derivatization, liquid carriers, hygroscopic materials, salts, wash solutions, blocking agents, reporter molecules, means for detecting the reporter molecule, a suitable flat, non-permable substrate, and one or more binding agents.

The components of the kits may be packaged either in aqueous media or in lyophilized form. When reagents and/or components are provided as a dry powder, the powder can be reconstituted by the addition of a suitable solvent. It is envisioned that the solvent may also be provided. Additionally, a substrate with a particle/bead pre-bound thereto also may be provided.

The container means of the kits will generally include at least one vial, test tube, flask, bottle, syringe or other container means, into which a component may be placed, and preferably, suitably aliquoted. Where there is more than one component in the kit, the kit also will generally contain a second, third or other additional containers into which the additional components may be separately placed. However, various combinations of components may be comprised in a vial. The kits of the present invention also will typically include a means for containing the reagent vials and other kit components in close confinement for commercial sale. Such containers may include injection or blow molded plastic containers into which the desired vials are retained.

Irrespective of the number or type of containers, the kits of the invention may also comprise, or be packaged with, instructions for use of the various reagents.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Particle functionalization and characterization.

Streptavidin-coated, monodisperse, superparamagnetic particles with a mean diameter of 1 µm were obtained from Life Technologies (P/N 656.01). Particles were washed three times with phosphate-buffered saline (PBS, pH 7.4) containing 0.01% Tween-20 and resuspended in the same buffer at a 10× dilution from the stock concentration. Mouse αM13 monoclonal antibody (1 mg/mL in PBS) was purchased from GE Healthcare (P/N 2792001) and biotinylated with biotinamidohexanoic acid N-hydroxysuccinimide ester purchased from Sigma Aldrich (P/N B2673). Unreacted ester groups were subsequently quenched with Tris buffer after a two-hour incubation period. Biotinylated antibody was added to the washed particle solution at an equivalent ratio of 1 mg antibody per 1 mL of stock particles. The particle solutions were then washed with PBS containing 0.01% Tween-20 three times following a two-hour incubation period. Free biotin was then added to the particle solution to bind any unreacted streptavidin on the surface of the particles. After 30 minutes, the particles were then washed three times and stored in PBS containing 0.005% Tween-20 and 0.005% bovine serum albumin (BSA). Control particles were prepared using the same base particle and by reacting with a molar excess of free biotin and then washing three times and storing in PBS with 0.005% Tween-20 and 0.005% BSA. The presence of conjugated antibody on the particles was confirmed by reacting the particles with a α-mouse secondary antibody/horseradish peroxidase conjugate (Sigma Aldrich, P/N A4416), washing three times, and then developing with 2,2'-azino-bis(3-ethylbenzothiazoline-6-sulphonic acid (ABTS) with hydrogen peroxide. This procedure was repeated for the control particles. Developed solutions turned green for the antibody-conjugated particles and remained clear for the control particles.

Immuno-Agglutination Assay Procedure.

Titration assays were carried out in small volume 72-well plates (Nunc, P/N 438733). Plates were first blocked with PBS containing 0.1% Tween-20 and 0.1% BSA, and then rinsed three times with PBS containing 0.1% Tween 20. M13 bacteriophage suspended in PBS was added to the plate and then serially diluted down the rows of the plate with PBS. An equal volume of particle solution containing $3 \times 10^6$ particles per µL (in PBS with 0.005% BSA and 0.005% Tween-20) was then added to each well and mixed. An equal volume of water containing 25% glycerol and 0.02% Tween 20 was then added to each well. The final concentration of particles and glycerol in the reaction volume was $1 \times 10^6$/nL and 8%, respectively. Particle solutions were allowed to react with M13 target for 30 min before depositing drops on the substrate for evaporation and image analysis.

Cross-Sectional Imaging Procedure.

A drop (1 µL) of reacted particle solution was deposited on a substrate, and cross-sectional images were recorded with optical coherence tomography (OCT). The procedure and experimental set-up were identical to a previously reported study using a commercial OCT system (Bioptigen, Inc.).[10] The experimental set-up resulted in an optical resolution of approximately 8 µm in the lateral direction, defined as the full-width half-max of the point-spread function of the system, and 6.4 µm in the axial direction. Transverse digital sampling resolution was 3 µm/pixel with an axial digital sampling resolution of 1.69 µm/pixel. OCT files were converted to tagged image file (TIFF) format in Matlab, and ImageJ software was used to edit video sequences and image stacks.

Drop Imaging Procedure and Signal Analysis.

Evaporated drops were imaged utilizing an Eclipse TE2000-U inverted microscope system (Nikon) with a 10× objective. The slide was front-illuminated using a 144 LED stereo microscopy light (AmScope). Images of the dried drops were captured using a Zyla sCMOS camera (Andor Technologies) and Elements AR software (Nikon Instruments). During capture, each drop was manually centerd in the field of view of the objective and manually focused using focus guides integrated into the software. Final images were captured in 11-bit greyscale at a capture resolution of 0.34 µm/pixel. All images were then processed in Elements to assess the aggregates delivered to the center of the drop. In order to account for variation in drop size, each drop was measured in Elements by creating a threshold mask of the drop and then measuring the size of the map in pixels. This data was then converted to an equivalent diameter which was used for normalization purposes during processing. After equivalent diameters were calculated, all images were cropped to 340 µm×340 µm and a circular region of interest with diameter of 340 µm was selected. This region was selected because it was large enough to encompass central aggregates for all drops, but small enough so as to exclude refraction artifacts occurring at the periphery. Particle identification was then performed on the cropped images with a brightness threshold set at the midpoint of the 11-bit brightness spectrum (luminosity ≥1024). In order to exclude free particles and only count aggregates, particle identification was further restricted to include only objects greater than 50 µm in size, a threshold determined in preliminary experiments. This process was performed identically on both αM13-functionalized particles and biotin control samples.

Data was processed by averaging all captured data for each sample at each concentration resulting in n=15 for each anti-M13 concentration (5 samples in triplicate) and n=3 (one sample in triplicate) for each biotin control sample. Total particle intensity and mean total particle area were taken from the output of the particle identification process for each drop. These values were normalized to drop size by dividing by drop diameter squared for total particle area and dividing by drop diameter cubed for total particle intensity. Overall means for each test concentration were then calculated as a ratio to mean values for the 0 pM test group and then limit of detection was determined using a logarithmic curve fit and interpolation to calculate the concentration at which projected area and intensity, respectively, would be three standard deviations above the 0 pM mean.

Example 2—Results

The assay design investigated here uses Marangoni flow to concentrate target-induced particle aggregates in the center of an evaporating drop. Unlike the primary radial flow that concentrates colloidal particles at the edge of the drop, the Marangoni flow in the assay reported here travels in the opposite direction and concentrates aggregated particles at the center of a drop forming an easily detectable spot. Design parameters including substrate material and solution components have been optimized to promote this center-directed Marangoni flow. FIG. 1A shows a cross-sectional representation of the theoretical Marangoni flow thought to be due to the temperature and surface tension gradients in a drop of evaporating solution (Hu & Larson, 2005). Fluid flows along the substrate toward the center of the drop then turns toward the air-water interface and flows in the direction of the contact line along the drop surface. The surface tension gradient from which these flow fields arise is thought to be caused by a temperature gradient that arises from cooling affects caused by the non-uniform evaporative flux along the drop surface. Originally described by Deegan, the evaporation rate of a drop is greatest at the contact line due to the proximal location of ambient, unsaturated gas resulting in non-uniform evaporation along the air-liquid interface (Deegan, 2000; Deegan et al., 2000; Deegan et al., 1997). The extent to which non-uniform evaporative cooling effects result in a temperature gradient along the drop surface is determined in part by the rate of heat transfer from the isothermal substrate to the air-liquid interface (Ristenpart et al., 2007). These heat transfer rates are, in part, a function of both the drop height as well as the thermal conductivities of the substrate and liquid. If the thermal conductivity of the substrate is sufficiently low, then evaporative cooling dominates and causes the lowest temperature to occur at the contact line. Conversely, a highly thermally conductive substrate promotes sufficient heat transfer at the contact line to overcome evaporative cooling effects resulting in the greatest temperature at the drop edge and lowest at the center. These temperature gradients cause surface tension gradients which in turn drive the Marangoni flow. According to Ristenpart et al., the drop is coolest at the contact line if the substrate has a thermal conductivity less than 1.45 times that of the liquid causing fluid to flow in the direction indicated in FIG. 1A (Bodiguel & Leng, 2012). If the substrate has a thermal conductivity greater than 2 times that of the liquid, the flow direction is reversed. The PDMS substrate used in the research reported here has a thermal conductivity of 0.15 W/mK, well below 1.45 times the liquid thermal conductivity (Eiermann, 1961). According to Ristenpart et al., the resulting flow direction should be the one shown in FIG. 1A. Moreover, these Marangoni flow fields are axisymmetric around the drop center resulting in a toroidal geometry when viewed from above the drop. FIG. 1B shows a three-dimensional rendering of these flow fields showing this symmetry around the drop center.

These internal flows and biomarker-induced aggregation are the two basic elements of this approach (FIGS. 2A-C). Particles (1 µm diameter) surface functionalized with monoclonal antibody that bind epitopes on the target biomarker either remain free in solution (FIG. 2A, left) or aggregate in the presence of the bacteriophage target (FIG. 2A, right). Particles become cross-linked in the presence of biomarker resulting in aggregate formation (FIG. 2A, right). When a drop of this solution is deposited on a PDMS substrate, Marangoni flow fields circulate particles in solution, shown in the cross section in FIG. 2C. In the absence of biomarker, particles follow these flow fields and are eventually deposited across the substrate surface, predominately at the drop edge resulting in a ring pattern (FIG. 2C, left). In the presence of biomarker, aggregated particles rapidly settle to the substrate and are then transported to the drop center by the Marangoni flow fields resulting in a concentrated spot (FIG. 2C, right). Due to non-specific particle binding events, a baseline amount of aggregated particles settle at the drop center in the absence of target biomarker and represents noise in the system.

The inventors have previously described a technique for visualizing cross-sectional flow fields in evaporating drops to characterize and optimize the motion of aggregates in the assay (Trantum et al., 2013). Optical coherence tomography (OCT) is a real-time, interferometry-based imaging modality in which objects are detected by measuring sample backscatter from a rastered source laser. With micrometer-scale axial and transverse resolution, millisecond temporal resolution, and a depth-of-field >1 mm, OCT is well-suited to the geometric and time constraints of flow fields in evaporating sessile drops (Trantum et al., 2013, Manukyan et al., 2013 and Drexler 2004). FIGS. 3A-B shows time-lapse composite images of an OCT scan through the diameter of a drop containing 0 pM of target (a) and 100 pM target (b). Each image spans 40 s and is generated by overlaying 200 sequential frames captured at a rate of five frames per second. Particles appear as white objects, and flow fields are visualized by the particle tracks that are generated in the composite image. Particles that have reacted with target biomarker in FIG. 3A are aggregated and therefore appear larger than the particles in FIG. 3B that do not have biomarker present. In both FIGS. 3A and 3B, the flow fields are in the direction noted in FIG. 1A and FIG. 2B, i.e., toward the contact line along the drop surface and toward the drop center along the substrate. This direction of motion is more apparent in the time sequence videos. These videos and the composite images in FIGS. 3A-B also show that the flow fields slow down throughout the evaporative process. As water evaporates, the glycerol contained in these drops steadily increases in concentration having the effect of slowing the evaporation rate which consequently reduces the surface tension gradient driving the Marangoni flow. This time-dependent change in glycerol also causes a changing refractive index with time. As a result, the OCT images in FIGS. 3A-B contain a shadowing effect at the early time points which is reduced as evaporation progresses. Glycerol is included in the drop solution in order to address the problem of salt crystallization that occurs upon complete evaporation of drops containing a physiologic concentration of salt (0.9%). In preliminary experiments, it was determined that this salt crystallization disrupts particle deposition patterns without glycerol. By including glycerol in the solution, drop evaporation ceases once the water vapor has completely evaporated leaving behind a residual amount of glycerol that prevents salt crystallization.

Importantly, FIG. 3A shows minimal aggregate accumulation at the center because the particles remain mostly monodisperse in the absence of biomarker. In this case, particles continue to circulate in the Marangoni flow. As the inventors have shown previously, some fraction of these particles becomes entrapped at the air-liquid interface due to surface tension effects and is eventually deposited at the contact line as a result of the outwardly directed flow field along the surface of the drop (Trantum et al., 2013). Other particles eventually settle along the substrate. FIG. 3B, however shows that large aggregates settle to the PDMS substrate and are transported to the drop center by the Marangoni flow where the particle aggregates become increasingly concentrated with time. This phenomenon is even more apparent in video sequences. Consequently, an evaporated drop of particle solution containing biomarker contains greater accumulation of particles at the center than if no biomarker is present. The final deposition pattern of a 'positive' contains a large spot in the center, which represents signal in the assay, and appears distinctively different from a 'negative.'

FIG. 4 shows phase contrast micrographs of these final deposition patterns at biomarker concentrations from 0 to 750 pM. The patterns shown in the right panel are a negative control at each corresponding biomarker concentration using particles with a non-reactive surface. These particles are the same as the functionalized particles used in the left panel except surface-coated with biotin rather than αM13 antibody and therefore do not aggregate in the presence of biomarker. The images in FIG. 4 show a general trend of increasing center spot size with increasing biomarker concentration with the smallest center spot occurring at 0 pM of biomarker. The deposition patterns at 0 pM biomarker appear essentially the same for the functionalized (left) and control (right). A small spot still appears at the 0 pM concentration due to baseline aggregation that results from non-specific binding between particles. To quantify this aggregation, particle size distributions in the absence and presence of varying amounts of biomarker were optically measured with phase contrast microscopy. This background noise could potentially be reduced in future designs by optimizing antibody conjugation techniques so as to maintain a monodisperse particle solution. Additionally, particle size and density parameters could be optimized to reduce this background noise.

Particles that do not aggregate are expected to accumulate at the drop edge. As a result, the ring structure should be larger in the 0 pM sample and biotin controls compared to the—αM13 samples containing M13 target. However, it is not possible to verify this expected result based on the images in FIG. 4 due to the refractive artifact that obscures the ring structure. This refractive artifact is caused by the residual glycerol and the underlying PDMS substrate. Since the particles are not fluorescent, but rather imaged under phase contrast light, it is difficult to characterize the final particle deposition patterns at the drop edge.

Signal in the assay was quantified by optically measuring the total area of aggregates in the center of the drop as defined by a region of interest (ROI) that was 0.6× the mean diameter of the drops (578 μm). This ROI size was chosen so as to exclude refractive artefact that occurs near the drop edge due to surface curvature of the fluid and refractive index of the residual glycerol. Signal measurements were subsequently normalized by the drop diameter to adjust for volume variations. Sample drops at each biomarker concentration were deposited in triplicate and signal measurements for the triplicates were averaged. A sample size of five was used in the study for a total number of fifteen drops at each biomarker concentration. Signal-to-noise was then calculated by normalizing assay signal by the baseline signal that is generated in the absence of biomarker. These data are plotted against biomarker concentration in FIG. 5A for both functionalized and control particles. The results show a concentration-dependent signal-to-noise for the functionalized particles that reaches a maximum value of 4.2 at approximately 28 pM of biomarker. Signal-to-noise from the control particles remains statistically indistinguishable from the 0 pM data point which indicates that particle aggregation in the assay is antibody-mediated. The signal-to-noise ratio of the antibody-functionalized particles decreases at greater concentrations of biomarker but remains more than three standard deviations above the zero at 750 pM of biomarker.

Signal in the assay increases when aggregated particles are transported by Marangoni flow fields into the center of the drop. With a fixed number of particles in solution, a greater biomarker concentration results in a greater mean aggregate size and a smaller fraction of unaggregated particles. However, this relationship reverses when available binding sites on the particles become saturated with biomarker. In this regime of biomarker concentration, aggregation is inhibited by the addition of biomarker because particles no longer compete for available binding sites making particle-particle cross-linking a less probable event. This previously described phenomenon, known as the Hook effect, is the reason why the signal-to-noise in FIG. 5A has a parabolic shape with respect to biomarker concentration (Fernando et al., 1992; Fernando et al., 1992). As a result, the dynamic range of the assay is limited to approximately four orders of magnitude under the experimental conditions used in this study. This limitation of the assay could potentially be improved in future designs by incorporating a range of antibody-to-particle ratios in the same particle solution. Preliminary data shows that this ratio significantly influences the size distribution of aggregated particles in a titration with biomarker. Additionally, the dynamic range of the proposed assay could be improved by evaporating an array of drops whereby the particle solution used in each drop has either a different antibody:particle ratio, or a fixed antibody:particle ratio with a different number of total particles.

Figure 5:
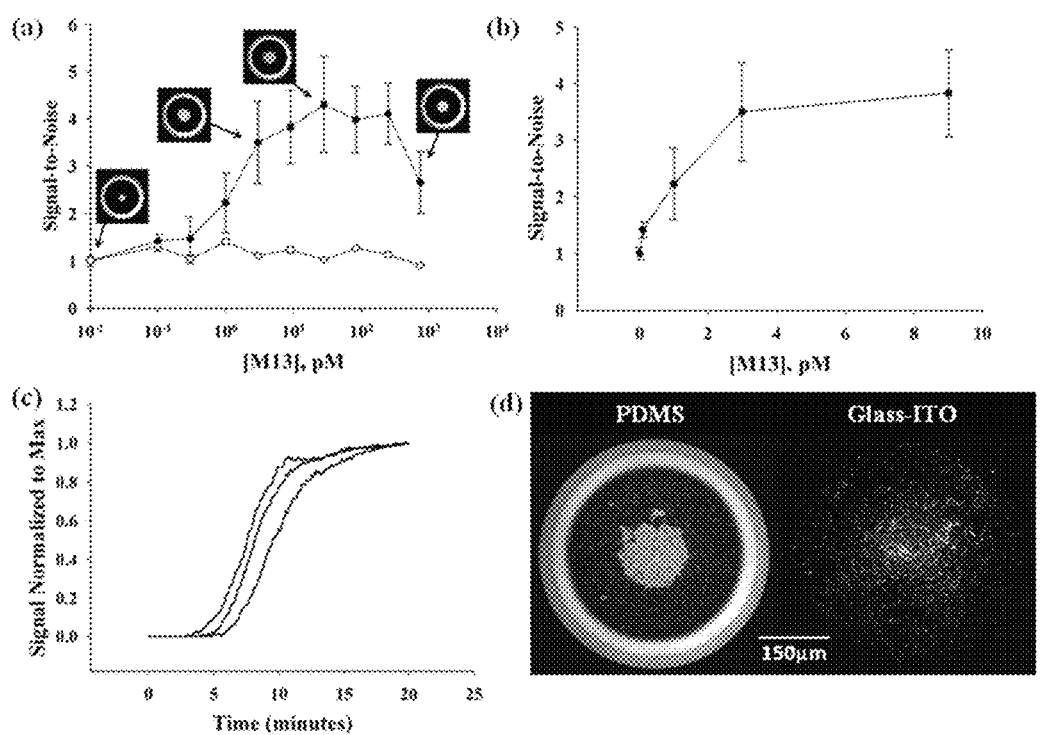
FIGS. 5A-D.
Figure 6:
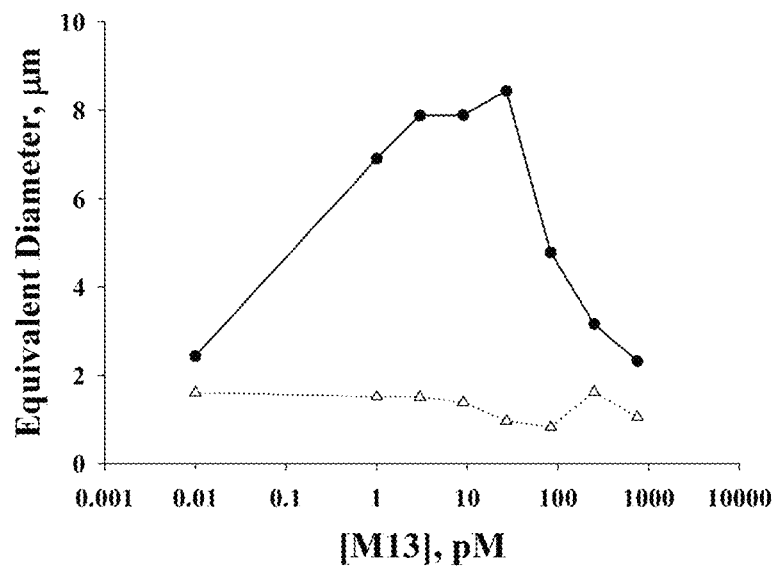
FIG. 6. Neutravidin-coated polystyrene particles (1 μm diameter, Invitrogen P/N F8775) were surface-functionalized with αM13 antibody and reacted with the M13 target at varying concentrations. Resulting aggregated particles were imaged with phase contrast microscopy and sized using Image Pro Plus software (v7.0). Mean equivalent diameter is plotted against M13 target concentration in a log-linear format.
Figure 7:
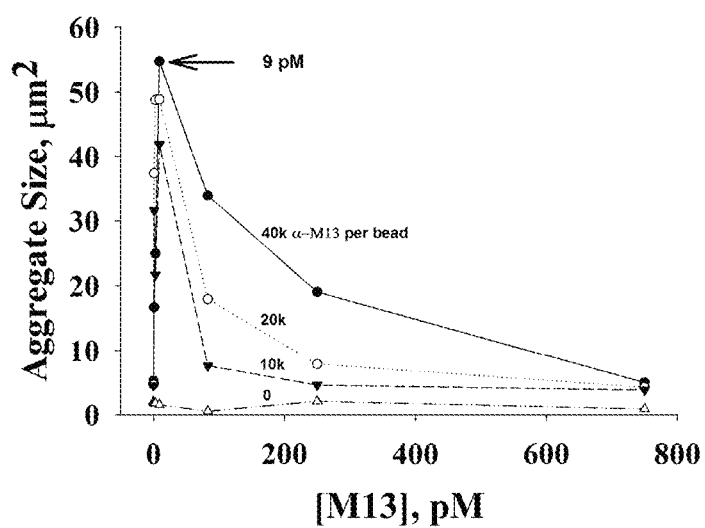
FIG. 7. Neutravidin-coated polystyrene particles (1 μm diameter, Invitrogen P/N F8775) were surface-functionalized with αM13 antibody at antibody:bead ratios of 40 k, 20 k, 10 k, and 0 and reacted with the M13 target at concentrations ranging from 750 pM to 0 pM. Resulting aggregated particles were sized using phase contrast microscopy. Mean aggregate area is plotted against M13 target concentration in a linear-linear format.
Figure 8:
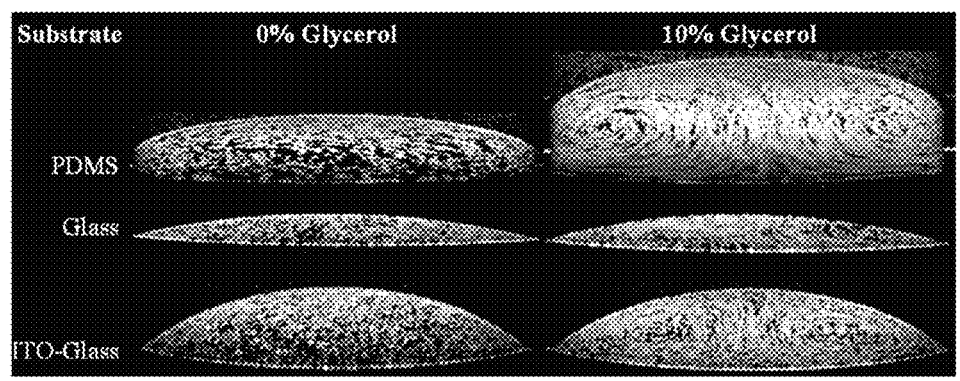
FIG. 8. The effects of glycerol and substrate composition on Marangoni flow were evaluated by depositing 1 μL drops of particle solutions containing $10^6$ polystyrene particles (1 μm diameter, carboxylated, Bangs Laboratories, Inc) on PDMS, glass, and an indium-tin oxide (ITO)-coated slide. Cross-sectional flow patterns were imaged with OCT through the diameter of the drop following a previously described protocol. Each time-lapse composite image consists of 200 consecutive OCT frames acquired at 5 fps.
Figure 9:
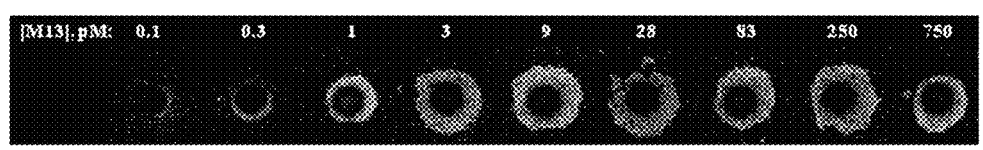
FIG. 9. Signal generated from varying amounts of M13 target as seen through a mask that subtracts the background noise from the signal. Background noise is the amount of particles that accumulate in the center of the drop in the absence of target.

The lower end of the signal-to-noise data from FIG. 5A is re-plotted in a linear-linear format in FIG. 5B. The limit of detection of the assay was determined by applying a second order curve fit to these data and calculating the lowest biomarker concentration at which signal-to-noise remains at least three standard deviations above the signal at 0 pM of biomarker. This approach indicates a limit of detection of 96 fM. Other methods of signal measurement, including total pixel intensity, number of objects, and mean object diameter, were also evaluated and found not to be as responsive to M13 target concentration as total aggregate area (data not shown).

Signal generation in the assay increases with time. As shown in FIG. 5C, Marangoni flow fields begin transporting settled aggregates to the center of the drop upon deposition on the PDMS substrate. These Marangoni flows persist until the evaporation-induced surface tension gradient along the surface of the drop is reduced as a result of increasing concentration of residual glycerol. As a result, signal-to-noise in the assay increases throughout drop evaporation and is quantitatively shown in FIG. 5C for three different drops. Signal-to-noise plotted against time shows an initial rise followed by a plateau. The rise is caused by the contribution of two different sources of signal: (1) transportation of aggregates to the center that have already settled on the substrate, and (2) aggregates circulating in the Marangoni flow that settle to the substrate at the drop center. The subsequent plateau in these data is due to the diminished flow fields that occur later in the evaporation process. A time sequence of phase contrast images provided in Supporting Information shows particle aggregates migrating to the center and the corresponding signal-to-noise as a function of time. The signal-to-noise reaches approximately 80% of maximum within 10 minutes of evaporation. It should be noted that 1 µL drop volumes were used in this study. Since the hydrodynamics scale with drop volume, the time constant of the assay could potentially be lowered by decreasing the drop volume. The trade-off would be detectability of the signal in the assay. At the 1 µL volume, the spot of aggregates that forms in the center of the assay is visually detectable. However, phase contrast microscopy was used in this study for more precise signal measurement. A likely field implementation of the design would rely on a smart phone to capture an image of the evaporated drop and use a locally-stored image processing app to interpret, quantify, transmit, and store the test result.

The substrate on which the sample drop is evaporated is an important design parameter. Ristenpart et al have conjectured that the presence and direction of Marangoni flow is dependent on the ratio of thermal conductivities of the substrate and drop fluid (Ristenpart et al., 2007). A drop of fluid placed on a substrate with sufficiently low thermal conductivity results in a temperature and surface tension gradient that promotes fluid flow along the drop surface directed toward the drop edge. Conversely, a high thermally conductive substrate causes flow in the reverse direction. Therefore, a substrate with sufficiently low thermal conductivity, like PDMS, is required to promote the Marangoni flow in the direction that concentrates biomarker-induced, aggregated particles at the drop center for detection. According to this theory, a substrate with sufficiently high thermal conductivity produces these flow fields in the opposite direction and therefore will not generate signal in the assay. For example, FIG. 5D shows the deposition patterns produced when a drop containing 28 pM of biomarker is evaporated on a PDMS substrate versus an indium tin oxide (ITO)-coated glass slide. The ITO-coated slide has a thermal conductivity of approximately 3.95 W/mK, significantly greater than the PDMS value of 0.15 W/mK and sufficiently thermally conductive to generate the reverse flow condition according to Ristenpart et al. (Ashida et al., 2009). Indeed, the final deposition pattern shown in FIG. 5D is more evenly spread-out along the substrate than that which results on PDMS. However, time composite OCT images of the flow fields that occur in a drop evaporating on an ITO-coated glass slide still show Marangoni flow in the same direction as that produced on a PDMS substrate. The Marangoni flow fields on the ITO slide occur at a much slower rate than PDMS, which explains the greater concentration of aggregated particles at the drop center on PDMS versus ITO. However, the reasons for this departure from the Marangoni flow conditions predicted by Ristenpart et al. are not entirely clear. Preliminary data show that a drop of particle solution in water evaporated on an ITO-coated slide does not produce Marangoni flow, but a drop of the same particle solution containing glycerol does produce Marangoni flow. In fact, the same observation was made for a PDMS substrate and on a regular glass slide to a lesser degree. The addition of glycerol to an aqueous solution may produce density and viscosity gradients in the evaporating drop that promote Marangoni flow in ways not incorporated in models reported to date.

Example 3—Discussion and Conclusion

As previously described, Marangoni flow in an evaporating drop refers to flow fields that result from a surface tension gradient at the air-liquid interface (Deegan, 2000, Deegan et al., 2000, Barash et al., 2009, Hu & Larson, 2005 and Hu & Larson, 2006). Deegan first postulated that the non-uniform evaporative flux across the surface of a drop necessarily leads to a corresponding temperature and surface tension gradient (Deegan, 2000; Deegan et al., 2000). This surface tension gradient, which is radially symmetric, causes fluid to flow from regions of low surface tension to high surface tension. Fluid transport across these temperature and surface gradients results in a cross-sectional flow current having toroidal geometry when viewing the drop from above. While this Marangoni flow is prevalent in organic solvents, previous studies have shown that it occurs minimally in aqueous drops presumably because the surface tension of an air-water interface is easily affected by the presence of trace exogenous materials (Hu & Larson, 2006). There have been conflicting reports about the effect of surfactants on Marangoni flow in evaporating drops. One study has shown the presence of surfactants to reduce the surface tension gradient and prevent Marangoni flow (Savino et al., 2002). Another group has shown a different type of surfactant molecule to promote Marangoni flow (Still et al., 2012). Drops in this study contain small amounts of the surfactant Tween 20, which may also contribute to the observed flow patterns.

Hu et al. have shown using a numerical simulation that the presence of Marangoni flow is dependent on the drop contact angle, which changes with evaporation time (Hu & Larson, 2005). They estimate that the surface tension-induced flow fields cease at contact angles below ~14°. This is thought to be due to the thermal conduction path to the isothermal substrate, which is the primary heat source, becomes sufficiently small at the drop center, and evaporative cooling at the edge is sufficiently large to eliminate the temperature and surface tension gradients at the drop surface.

Physical and chemical properties of an evaporating drop, like contact angle, non-uniform evaporation rates, and material concentrations, are dynamic and interdependent. Chemical, density, viscosity, temperature, density, and surface tension gradients change with evaporation time and likely affect Marangoni flow fields in ways that are not well understood. These phenomena are the focus of on-going studies.

The design parameters used in this initial biosensor design were chosen to demonstrate proof-of-concept for a low resource point-of-care assay. Several system variables could be optimized for specific future applications. Since the design uses an antibody as the biorecognition element, the assay could be adapted to many different disease types. Here, the inventors use the M13K07 bacteriophage as a model target. The bacteriophage, commonly used for phage display, is a cigar-shaped viral capsid approximately 700 nm in length with 2,800 surface-bound epitopes. The M13 bacteriophage a good cross-linking agent likely to induce aggregation in the assay because it has a length similar to the diameter of the functionalized particles used in the assay as well an abundance of binding sites. The calculated limit of detection of the assay may be different for different types of biorecognition elements and targets. The biosensor could generate a colorimetric signal by incorporating dyed or fluorescent particles. Assay limit of detection and dynamic range may be tuned by optimizing particle size, concentration, and density for a given disease application. The assay design could be further improved by comparing the test result to a control spot and/or evaporating the drop on a functionalized surface that would capture the aggregated particles and enable a rinse step to remove background materials that may obfuscate test interpretation (e.g., red blood cells). Finally, the effects of glycerol and surfactant concentrations have not yet been fully elucidated and may be further modified to improve overall biosensor performance. The biosensor investigated in this study has the advantage of using a polydimethylsiloxane (PDMS) substrate, which is commonly used in microfluidics (Folch et al., 1999). Therefore, this design could potentially be integrated with existing PDMS-based microfluidic architectures, for example droplet-based microfluidic devices. These devices use electrowetting techniques to manipulate the motion and processing of drops on a PDMS surface (Teh et al., 2008 and Cho et al., 2003). The approach presented here could potentially be integrated with such technology to provide an optically detectable, multiplexed, and quantifiable test read-out strategy.

In conclusion, this work demonstrates the utility of a biosensor design that relies on the hydrodynamics of an evaporating drop to generate an optically detectable test result. This study shows that antibody-functionalized particles aggregate in the presence of biomarker and when a drop of this solution is evaporated on a PDMS substrate, Marangoni flows concentrate the aggregates at the center of the drop. The substrate material and solution conditions are important design parameters that affect the dynamics of the evaporation-induced flow fields and the extent to which aggregated particles become concentrated in the drop. Signal in the assay is based on the spatial distribution of particle depositions upon drop evaporation. Using standard microscopy to measure the test result, a femtomolar limit of detection is achievable. Future designs may incorporate a camera phone for signal measurement and interpretation, which would be more amenable to a point-of-care diagnostic useful in a low resource setting.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VII. References

The following references, to the extent that they provide exemplary procedural or other details supplementary to those set forth herein, are specifically incorporated herein by reference.

Ashida et al., *J Appl Phys*, 105, (7), 2009.
Barash, et al., *Physical Review E*, 79, (4), 2009.
Barton et al., *ICONN*, 2006.
Bodiguel & Leng, *Chemical Engineering and Processing: Process Intensification* 2012.
Bodiguel & Leng, *Soft Matter*, 6, (21), 5451-5460, 2010.
Brinas et al., *J Am Chem Soc*, 130, 975-982, 2008.
Brutin et al., *Journal of Fluid Mechanics*, 667, 85-95, 2011.
Chiodini et al., *Trans R Soc Trop Med Hyg*, 101, 331-7, 2007.
Cho et al., *J Microelectromech S*, 12, (1), 70-80, 2003.
De et al., *Macromol Biosci*, 9, 174-8, 2009.
Deegan et al., *Nature*, 389, (6653), 827-829, 1997.
Deegan et al., *Nature*, 389, 827-829, 1997.
Deegan et al., *Physical Review E*, 62, (1), 756-765, 2000.
Deegan, *Physical Review E*, 61, (1), 475-485, 2000.
Drexler, *Journal of Biomedical Optics*, 9, (1), 47-74, 2004.
Eiermann, *Kunststoffe*, 51, (9), 512-517, 1961.
Fatenejad, *J. Immunol.*, 152:5523-5531, 1994.
Fernando, et al., *Journal of immunological methods*, 151, (1-2), 27-46, 1992.
Fernando, et al., *Journal of immunological methods*, 151, (1-2), 47-66, 1992.
Folch, et al., *J Biomech Eng-T Asme*, 121, (1), 28-34, 1999.
Gay et al., *Trans R Soc Trop Med Hyg*, 90, 516-8, 1996.
Ghimire et al., *Southeast Asian J Trop Med Public Health*, 34, 739-43, 2003.
Gupta et al., *Bioconjugate Chemistry*, 19, 1964-1967, 2008.
Hoet et al., *J. Immunol.*, 163:3304-3312, 1999.
Hu et al., *Langmuir*, 21, (9), 3972-3980, 2005.
Hu et al., *Journal of Physical Chemistry B*, 110, (14), 7090-7094, 2006.
Hu et al., *Langmuir*, 21, (9), 3963-3971, 2005.
Lauer & Nolan, *Cytometry*, 48, 136-45, 2002.
Lee et al., *Langmuir*, 25, 657-660, 2009.
Lotz et al., *Mol. Biol. Rep.*, 16:127, 1992.
Magnusson et al., *Scand. J. Immunol.*, 54:543-550, 2001.
Malmegrim et al., *Isr. Med. Assoc. J.*, 4:706-712, 2002.
Manukyan, et al., *Journal of Colloid and Interface Science*, 395, 287-293, 2013.
Mohan et al., *J. Exp. Med.*, 177:1367-1381, 1993.
Newkirk et al., *Arthritis Res*, 3:253-258, 2001.
Panton et al., *Mol Biochem Parasitol*, 35, 149-60, 1989.
Ristenpart et al., *Physical Review Letters*, 99, (23), 2007.
Sangani et al., *Physical Review E*, 80, (1), 2009.
Savino et al., *Journal of Thermophysics and Heat Transfer*, 16, (4), 562-574, 2002.
Still etr al., *Langmuir*, 28, (11), 4984-4988, 2012.
Tarasevich et al., *European Physical Journal E*, 22, (4), 311-314, 2007.
Tarasevich et al., *Technical Physics*, 52, (2), 159-163, 2007.
Teh, et al., *Lab on a Chip*, 8, (2), 198-220, 2008.
Trantum et al., *Langmuir*, 28, (4), 2187-2193, 2012.
Trantum et al., *Langmuir*, 29, (21), 6221-31, 2013.
Vallin et al., *J. Immunol.*, 163:6306-6313, 1999.
ven Venrooij, *J. Clin. Invest.*, 86:2154-2160, 1990.
Wong et al., *Analytical Chemistry*, 83, (6), 1871-1873, 2011.
world-wide-web at gatesfoundation.org/topics/Pages/malaria.aspx
Yager, et al., *J. Annu Rev Biomed Eng*, 10, 107-44, 2008.
Yager, et al., *Nature*, 442, (7101), 412-418, 2006.

What is claimed is:

1. A method for detecting an analyte in a sample comprising:
   (a) providing said sample in an aqueous liquid carrier, said liquid carrier also comprising (i) a salt or a sugar (ii) and a hygroscopic material and/or a surfactant;
   (b) contacting said sample of step (a) with a capture particle that binds an analyte in said sample, wherein the presence of analyte results in cross-linking of said capture particles;
   (c) placing a droplet of said sample of step (b) on a non-permeable substrate made of plastic or polydimethylsiloxane, wherein the thermal conductivity of the substrate is less than 2 times that of the liquid sample, and the substrate is characterized by a contact angle resulting in a hydrophobic state;

(d) incubating said substrate under conditions promoting sustained Marangoni flow in said droplet in which the sustained Marangoni flow is symmetric about the center of the droplet and has a direction that is toward the center of the droplet along the substrate and toward the edge of the droplet along the liquid/air interface; and (e) detecting the analyte, wherein the presence of cross-linked capture particles at said droplet center, as compared to a control assay lacking said analyte, reflects the presence of analyte in said sample.

2. The method of claim 1, wherein said capture particle comprises an analyte binding agent selected from a protein, a chemical, a nucleic acid, a metal, and a carbohydrate.

3. The method of claim 1, wherein said non-permeable substrate is a plastic slide, a polydimethylsiloxane slide, a plastic rod, a plastic capillary tube, or a microarray pen.

4. The method of claim 1, wherein said analyte is a protein, a nucleic acid, a toxin, a lipid, a carbohydrate, a drug or chemical, or a metal.

5. The method of claim 1, wherein said liquid carrier comprises water or organic solvent.

6. The method of claim 1, wherein said sample is a foodstuff, water, soil, plant material, a biopsy, bronchial lavage, nasal lavage, nasal swab, cheek swab, or a body fluid.

7. The method of claim 1, further comprising washing said non-permeable substrate after step (d).

8. The method of claim 1, further comprising adding a detection agent that detects (i) said capture particle bound to said analyte at said droplet center or (ii) analyte at said droplet center.

9. The method of claim 1, wherein said capture particles exhibit a detectable change when cross-linked.

10. The method of claim 1, wherein said capture particle is labeled.

11. The method of claim 1, wherein said non-permeable substrate is derivatized to bind said capture particle or said analyte.

12. The method of claim 1, wherein said capture particles are located on said non-permeable substrate, and steps (b) and (c) are comprised in a single step of dropping said sample onto said non-permeable substrate.

13. The method of claim 1, wherein steps (b) and (c) are reversed in order.

14. The method of claim 1, further comprising performing a positive control reaction using a control particle.

15. The method of claim 1, wherein said capture particles further comprise an agent that reduces non-specific binding to other reagents.

16. The method of claim 1, wherein multiple droplets are placed on said substrate.

17. A method for detecting an analyte in a sample comprising:

(a) mixing the sample with capture particles that bind an analyte in said sample;

(b) contacting said sample with an aqueous liquid carrier also comprising (i) a salt or a sugar (ii) and a hygroscopic material and/or a surfactant;

(c) placing a droplet of said sample in step (b) on a non-permeable substrate made of plastic or polydimethylsiloxane, wherein the thermal conductivity of the substrate is less than 2 times that of the liquid sample, and the substrate is characterized by a contact angle resulting in a hydrophobic state;

(d) incubating said substrate under conditions promoting sustained inward Marangoni flow in said droplet; and (e) detecting the analyte, wherein the presence of capture particles at said droplet center, as compared to a control assay lacking said analyte, reflects the presence of analyte in said sample.

18. A method for detecting an analyte in a sample comprising:

(a) providing a sample receptacle containing (i) capture particles that bind an analyte in said sample, (ii) a salt or a sugar and (iii) a hygroscopic material and/or a surfactant;

(b) disposing a sample into said sample receptacle;

(c) placing a droplet of said sample in step (b) on a non-permeable substrate made of plastic or polydimethylsiloxane, wherein the thermal conductivity of the substrate is less than 2 times that of the liquid sample, and the substrate is characterized by a contact angle resulting in a hydrophobic state;

(d) incubating said substrate under conditions promoting sustained inward Marangoni flow in said droplet; and (e) detecting the analyte, wherein the presence of capture particles at said droplet center, as compared to a control assay lacking said analyte, reflects the presence of analyte in said sample.

* * * * *

UNITED STATES PATENT AND TRADEMARK OFFICE
CERTIFICATE OF CORRECTION

PATENT NO. : 10,101,323 B2  
APPLICATION NO. : 14/520541  
DATED : October 16, 2018  
INVENTOR(S) : Frederick Haselton et al.

Page 1 of 1

It is certified that error appears in the above-identified patent and that said Letters Patent is hereby corrected as shown below:

In the Specification

In Column 1, Lines 8-11, please delete the paragraph and insert:
--This invention was made with government support under Grant nos. EB009235, EY017522, and HL095119 awarded by the National Institutes of Health. The government has certain rights to this invention.-- therefor.

Signed and Sealed this  
Twenty-sixth Day of September, 2023

Katherine Kelly Vidal  
*Director of the United States Patent and Trademark Office*